(12) United States Patent
Kim

(10) Patent No.: US 8,791,993 B2
(45) Date of Patent: Jul. 29, 2014

(54) MEDICINE MANAGEMENT SYSTEM AND METHOD USING THE SAME

(75) Inventor: Jun-Ho Kim, Daegu (KR)

(73) Assignee: JVM Co., Ltd. (KR)

( * ) Notice: Subject to any disclaimer, the term of this patent is extended or adjusted under 35 U.S.C. 154(b) by 723 days.

(21) Appl. No.: 12/977,378

(22) Filed: Dec. 23, 2010

(65) Prior Publication Data

US 2011/0157342 A1    Jun. 30, 2011

(30) Foreign Application Priority Data

Dec. 30, 2009  (KR) .................. 10-2009-0134416
Dec. 30, 2009  (KR) .................. 10-2009-0134420
Mar. 8, 2010   (KR) .................. 10-2010-0020480

(51) Int. Cl.
| | | |
|---|---|---|
| H04N 7/18 | (2006.01) | |
| G06K 9/00 | (2006.01) | |
| G06F 19/00 | (2011.01) | |
| G06F 7/00 | (2006.01) | |

(52) U.S. Cl.
CPC ............... *H04N 7/18* (2013.01); *G06F 19/00* (2013.01); *G06F 7/00* (2013.01)
USPC ............................................. 348/61; 382/128

(58) Field of Classification Search
None
See application file for complete search history.

(56) References Cited

U.S. PATENT DOCUMENTS

| | | | | |
|---|---|---|---|---|
| 4,574,393 | A  * | 3/1986  | Blackwell et al. | 382/162 |
| 4,974,249 | A  * | 11/1990 | Zweig | 378/190 |
| 5,459,605 | A  * | 10/1995 | Kempf | 359/462 |
| 6,916,221 | B2 * | 7/2005  | Kaltenbach et al. | 445/3 |
| 2004/0220767 | A1 * | 11/2004 | Tanaka et al. | 702/127 |
| 2005/0088542 | A1 * | 4/2005  | Stavely et al. | 348/239 |
| 2006/0033824 | A1 * | 2/2006  | Nicholson | 348/265 |
| 2006/0271237 | A1 * | 11/2006 | Kim | 700/226 |
| 2008/0013820 | A1 * | 1/2008  | Vertoprakhov et al. | 382/141 |
| 2008/0285840 | A1 * | 11/2008 | Kawai | 382/141 |
| 2010/0094653 | A1 * | 4/2010  | Tribble et al. | 705/3 |

* cited by examiner

*Primary Examiner* — Nhon Diep
*Assistant Examiner* — Edemio Navas, Jr.
(74) *Attorney, Agent, or Firm* — Cantor Colburn LLP

(57) ABSTRACT

Disclosed herein is a medicine management system wherein a camera is installed in a camera tube to acquire a good-quality medicine image, thereby improving recognition efficiency. A method of setting the camera of the medicine image capturing device includes extracting a jig block from a medicine image captured by the medicine image capturing device, analyzing image elements of the jig block, and setting a capturing mode of the camera.

10 Claims, 28 Drawing Sheets

Fig. 16
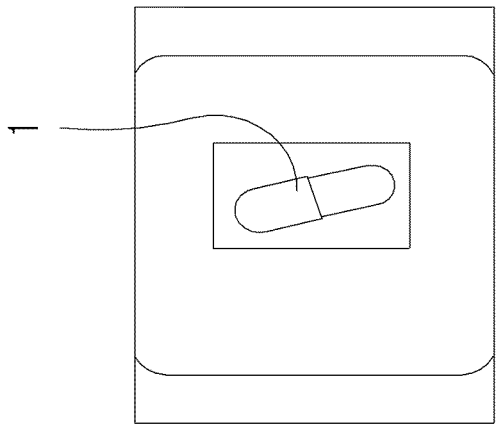
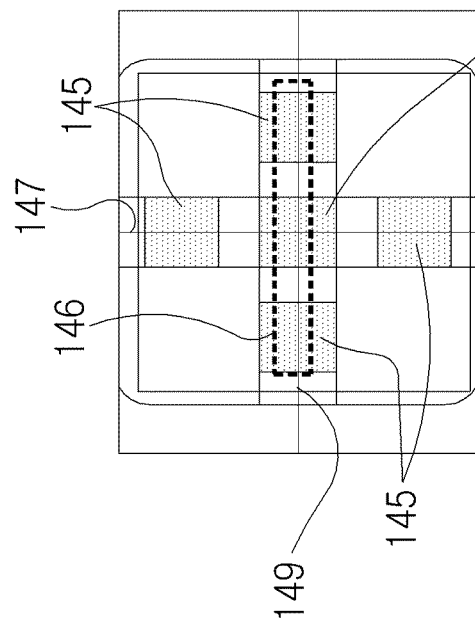
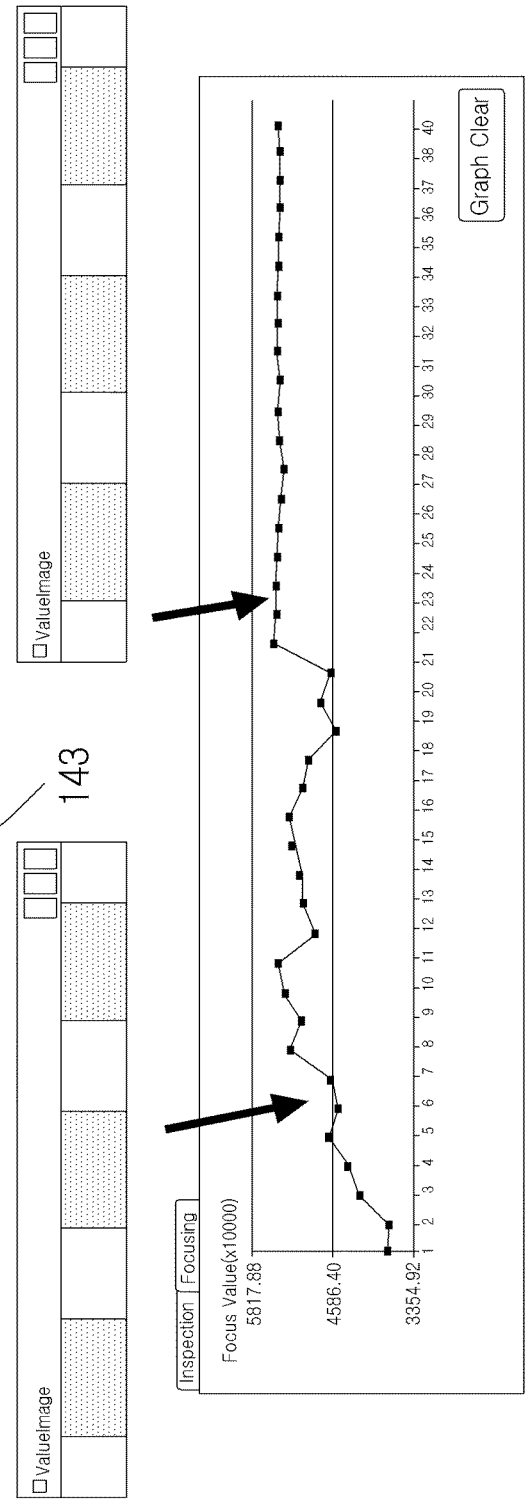

(a)　　　　(b)

Fig. 31
(a)
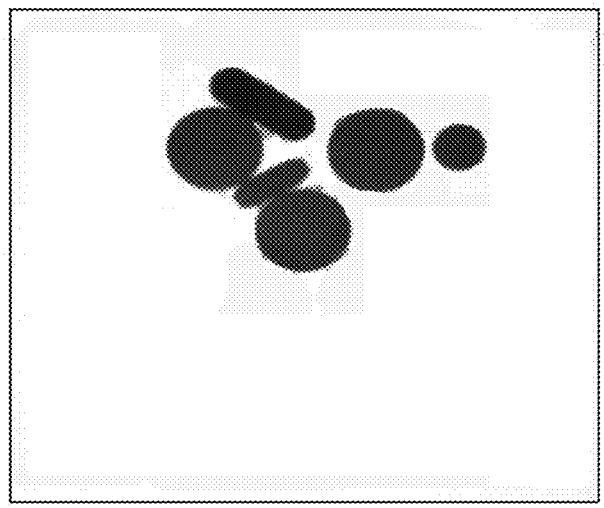
GRAY INPUT IMAGE
(b)
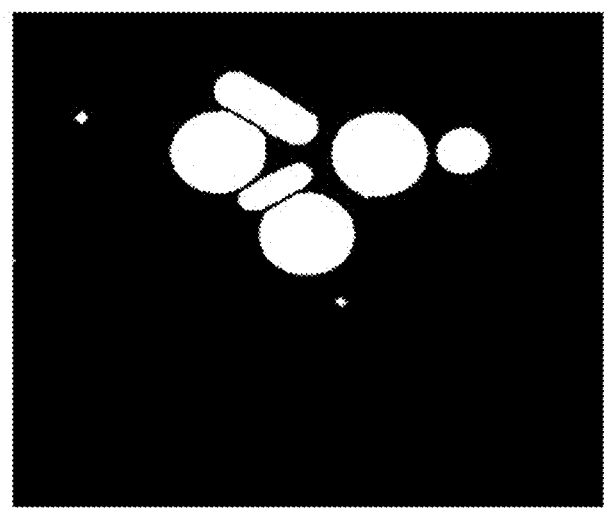
SEPARATED MEDICINE IMAGE

MEDICINE MANAGEMENT SYSTEM AND METHOD USING THE SAME

BACKGROUND OF THE INVENTION

1. Field of the Invention

The present invention relates to a medicine management system and method that capture and analyze an image of an individual medicine using the medicine image capturing device to calculate and manage medicine pattern information, thereby improving efficiency in management of individual medicine information and determining whether a compound medicine is abnormal.

2. Description of the Related Art

In recent years, medicines have been diversified, and the amount of the medicines has been vastly increased. As a result, it is necessary to provide a system that is capable of managing medicine information in a batch manner in places where various kinds of medicines are managed, such as large-scale pharmacies and dispensaries of hospitals.

However, hospitals and pharmacies have different medicine management codes. In addition, nations have different medicine management codes. That is, medicine retrieval criteria are not standardized. As a result, it is difficult to efficiently manage medicine information.

Also, a large number of human resources are needed to determine whether a medicine compounding state is normal per packaged medicine in hospitals and pharmacies where a large amount of compound medicines is managed. Furthermore, such determination needs a long test time.

Also, it is not possible to easily determine errors of medicines having identical or similar color or size, and therefore, defects of compound medicines may lower effects of patient treatment. In addition, defects of compound medicines may have a bad effect on patient health.

For these reasons, various kinds of medicine information management devices that are capable of capturing and analyzing medicine images to calculate medicine pattern information have been developed. Also, devices that are operatively connected to the medicine information management devices for automatically testing compound medicines have been developed.

It is possible for each of the automatic compound medicine testing devices to capture images of the compound medicines and compare the captured compound medicine images with medicine image information stored in each of the medicine information management devices to determine whether the captured compound medicine images coincide with the medicine image information stored in each of the medicine information management devices.

At the time of operative connection between each medicine information management device and each compound medicine testing device, however, camera setting values based on image capturing may not be synchronized, with the result that incongruity errors on the same medicine information may frequently occur during testing.

Also, persons in charge who manage the medicine information management devices and the compound medicine testing devices may differently set the camera setting values, with the result that the camera setting values may be different between the medicine information management devices and the compound medicine testing devices, thereby lowering efficiency of medicine information management.

Also, in each of the conventional compound medicine testing devices, an image capturing camera is exposed to the outside, with the result that quality of medicine images is greatly affected by the external environment.

SUMMARY OF THE INVENTION

Therefore, the present invention has been made in view of the above problems.

In one aspect of the present invention, it is an object of the present invention to provide a medicine image capturing device wherein a camera is installed in a camera tube, thereby acquiring a good-quality medicine image and easily adjusting camera setting values.

It is another object of the present invention to provide a medicine image capturing device wherein a reflection plate is provided at a refraction plane of the camera tube to secure the working distance between a medicine loading table and the camera, thereby preventing distortion of a medicine shape which occurs when the working distance is short.

It is another object of the present invention to provide a medicine image capturing device wherein a camera module is configured in a bent shape such that the camera module can be installed in a limited equipment space, thereby improving spatial utilization.

It is another object of the present invention to provide a medicine image capturing device wherein a correction panel is further provided to easily standardize camera setting values.

It is another object of the present invention to provide a medicine image capturing device wherein a jig block is included in the correction panel, thereby easily testing the camera setting values.

It is another object of the present invention to provide a medicine image capturing device wherein a center jig block and an auxiliary jig block are included in the correction panel, thereby easily analyzing camera setting elements at each position.

It is another object of the present invention to provide a medicine image capturing device wherein a camera setting unit is further included to test and adjust the camera setting elements.

It is a further object of the present invention to provide a medicine image capturing device that is capable of analyzing a focus, an image center axis, an image scale, and intensity of the camera.

In another aspect of the present invention, it is an object of the present invention to provide a medicine management system that is capable of calculating and managing medicine pattern information based on medicine image analysis, thereby efficiently managing a large amount of medicine information, and is capable of determining whether compound medicines are normal, thereby decreasing a defect rate of medicine compounding and improving management of the compound medicines.

It is another object of the present invention to provide a medicine management system wherein a medicine shift arrangement unit is further included to adjust positions or directions of medicines, thereby providing a function to capture the medicines in various directions and rapidly performing barcode recognition, capturing of compound medicines, and label attachment.

It is another object of the present invention to provide a medicine management system wherein basic medicine information, pattern information and medicine image information are stored in a storage unit, thereby configuring systematic medicine information.

It is another object of the present invention to provide a medicine management system that is capable of analyzing various medicine pattern elements, such as external shape, color, marking, external dimensions, etc.

It is another object of the present invention to provide a medicine management system wherein a basic information input unit is further included to provide a function to input basic information of medicines.

It is another object of the present invention to provide a medicine management system wherein a medicine information retrieval unit is further included to easily retrieve basic medicine information using medicine pattern information.

It is another object of the present invention to provide a medicine management system wherein an identification code recognition unit is further included to recognize an identification code formed on compound medicine packaging paper, thereby improving efficiency in retrieval of medicine compounding information of medicines.

It is another object of the present invention to provide a medicine management system that is capable of analyzing and storing basic information and pattern information per medicine to compare pattern information of the captured medicine image with the pattern information per medicine.

It is another object of the present invention to provide a medicine management system wherein a label creation unit is further included to create and attach a label indicating whether a compound medicine per package is abnormal, thereby easily recognizing defective compound medicines.

It is another object of the present invention to provide a medicine management system that is capable of determining whether compound medicines are defective based on various kinds of information, such as size, quantity and shape, of medicines, thereby improving accuracy of compound medicine testing.

It is a further object of the present invention to provide a medicine management system wherein a rearrangement unit for shaking overlapped medicines or the medicines placed in incorrect capturing directions in each medicine package to rearrange the overlapped medicines or the medicines placed in incorrect capturing directions is included in the medicine shift arrangement unit.

In a further aspect of the present invention, it is an object of the present invention to provide a medicine management method that is capable of performing a medicine pattern information registration operation using a medicine image, thereby improving medicine information management, and is capable of determining whether compound medicines are defective, thereby reducing time necessary to test the compound medicines and improving accuracy of testing.

It is another object of the present invention to provide a medicine management method that is capable of setting a camera for capturing a medicine image, thereby improving efficiency and accuracy in processing of the medicine image.

It is another object of the present invention to provide a medicine management method that is capable of setting components of an image capturing device unit in advance.

It is another object of the present invention to provide a medicine management method that is capable of extracting a jig block from a collected correction panel image.

It is another object of the present invention to provide a medicine management method that is capable of measuring the center coordinates and scale of a center jig block.

It is another object of the present invention to provide a medicine management method that is capable of testing intensity of a correction panel image using an auxiliary jig block.

It is another object of the present invention to provide a medicine management method that is capable of comparing a medicine image with a correction panel image, thereby determining whether defined camera setting values are proper.

It is another object of the present invention to provide a medicine management method that is capable of acquiring a color image and a black-and-white image using a single capturing unit by adjusting brightness of illumination.

It is another object of the present invention to provide a medicine management method that is capable of calculating pattern information based on shapes of the medicines and expressing the calculated pattern information of the medicines as a graph or a shape code which is visually distinguishable.

It is another object of the present invention to provide a medicine management method that is capable of registering medicine images captured in various directions, thereby improving accuracy in retrieval of medicine information.

It is another object of the present invention to provide a medicine management method that is capable of standardizing medicine color information acquired in the form of a color image, thereby improving accuracy of medicine retrieval and recognition.

It is another object of the present invention to provide a medicine management method that is capable of calculating marking information of the medicines as pattern information, thereby improving accuracy of medicine retrieval and recognition.

It is another object of the present invention to provide a medicine management method that is capable of registering medicine information of medicines cut into various sizes, thereby improving accuracy of medicine information retrieval per medicine package.

It is another object of the present invention to provide a medicine management method that is capable of recognizing an identification code formed on an individual medicine package, thereby easily retrieving medicine compounding information.

It is another object of the present invention to provide a medicine management method that is capable of creating a black-and-white medicine image as well as a color medicine image, thereby easily analyzing individual regions of the medicines.

It is another object of the present invention to provide a medicine management method that is capable of analyzing a medicine image into independent regions of individual medicines, thereby easily deriving pattern information of the individual medicines.

It is another object of the present invention to provide a medicine management method that is capable of deriving and comparing histogram information of the captured medicines based on external shape thereof with medicine compounding information.

It is another object of the present invention to provide a medicine management method that is capable of attaching a defective state indicating label, upon determining that the size and quantity of the captured medicine or the histogram information of the captured medicines based on external shape thereof does not coincide with the medicine compounding information, thereby easily recognizing defective medicines.

It is another object of the present invention to provide a medicine management method that further includes an illumination adjusting step, thereby easily recognizing an identification code formed on medicine packaging paper.

It is a further object of the present invention to provide a medicine management method that further includes a step of confirming a captured state of the acquired medicine image to rearrange medicines analysis of which is not possible, thereby improving efficiency of image analysis.

In accordance with one aspect of the present invention, the above and other objects can be accomplished by the provision of a medicine image capturing device including a camera tube having a refraction plane formed therein at a predetermined point thereof so that a predetermined angle is defined between one side and the other side of the camera tube and a camera disposed in the camera tube at one side thereof for capturing medicines.

In accordance with another aspect of the present invention, there is provided a medicine management system including an image capturing device unit comprising a camera tube having a refraction plane formed therein at a predetermined point thereof so that a predetermined angle is defined between one side and the other side of the camera tube and a camera disposed in the camera tube at one side thereof for capturing medicines, an image analysis unit for analyzing a medicine image captured by the image capturing device unit, a medicine pattern analysis unit for calculating medicine pattern information based on the medicine image analyzed by the image analysis unit, and a medicine management control unit connected to the image analysis unit and the medicine pattern analysis unit for managing the medicine pattern information and determining whether compound medicines are abnormal.

In accordance with a further aspect of the present invention, there is provided a medicine management method including setting a camera of an image capturing device unit, registering medicine information of a medicine image captured by the image capturing device unit, and comparing medicine information of a compound medicine image captured by the image capturing device unit with registered medicine information to determine whether the compound medicine is abnormal.

BRIEF DESCRIPTION OF THE DRAWINGS

The above and other objects, features and other advantages of the present invention will be more clearly understood from the following detailed description taken in conjunction with the accompanying drawings, in which:

FIGS. 12, 13 and 15 to 17 are views illustrating an embodiment of a program corresponding to Step S131 to Step S160 of the medicine management method according to the present invention;

FIGS. 29 and 31 are views illustrating an embodiment of Step S340 and Step S350 of the medicine management method according to the present invention.

DETAILED DESCRIPTION OF THE INVENTION

Now, preferred embodiments of the present invention will be described in detail with reference to the accompanying drawings.

First, a medicine image capturing device according to the present invention will be described in detail.

Figure 1:
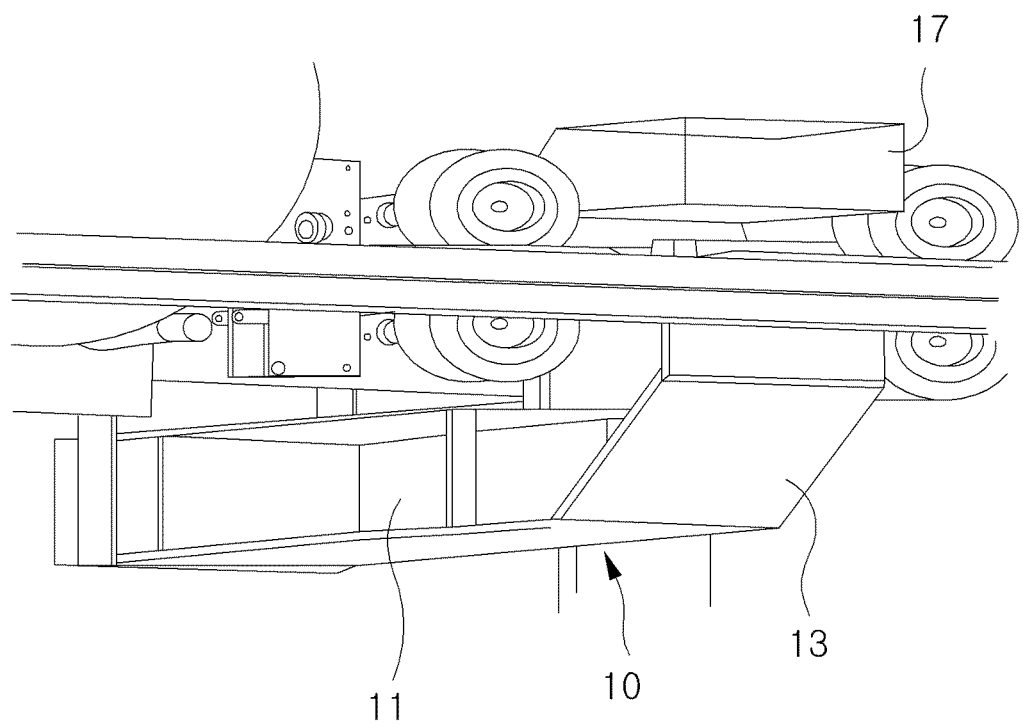
FIG. 1 is a perspective view illustrating an embodiment of a medicine image capturing device according to the present invention.
Figure 2:
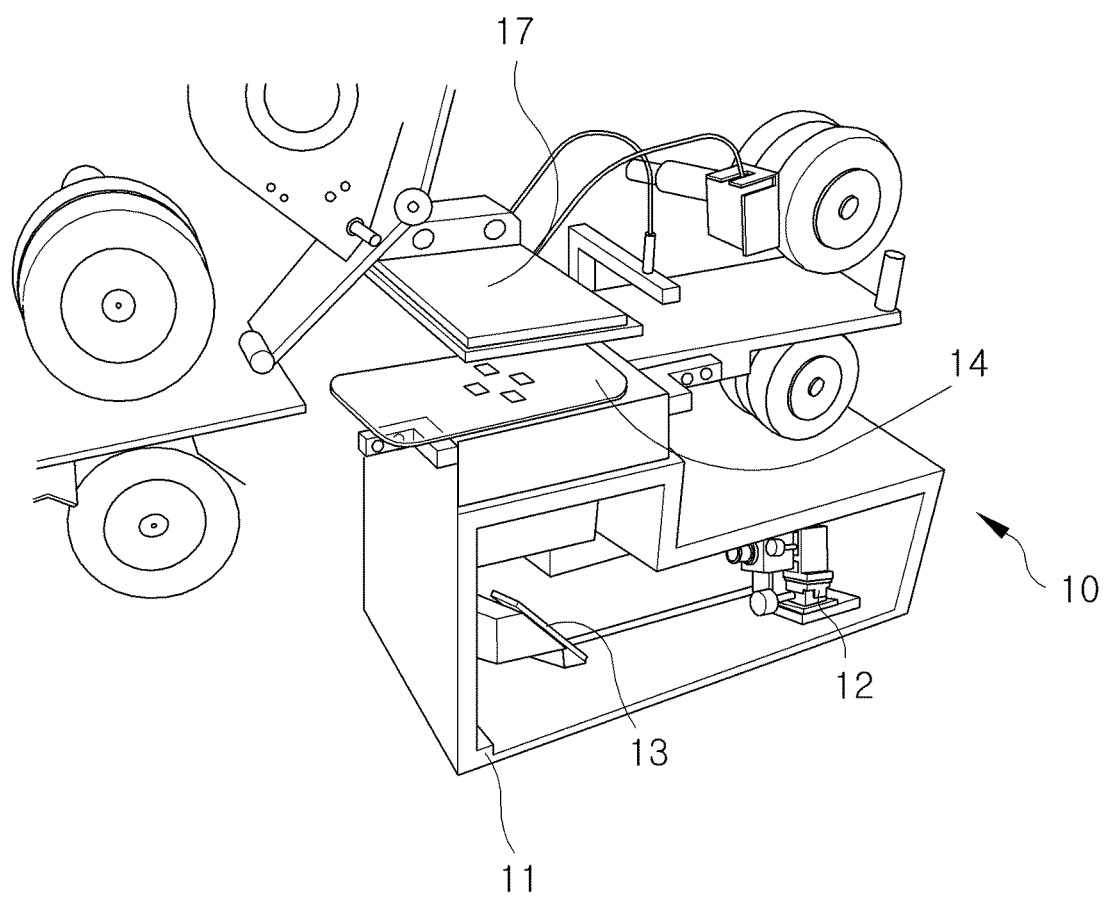
FIG. 2 is a perspective view illustrating the interior of the medicine image capturing device according to the present invention.

FIG. 1 is a perspective view illustrating an embodiment of a medicine image capturing device 10 according to the present invention, and FIG. 2 is a perspective view illustrating the interior of the medicine image capturing device 10 according to the present invention. The medicine image capturing device 10 includes a camera tube 11, a camera 12, a reflection plate 13, a correction panel 14, and an illumination unit 17.

In the medicine image capturing device 10 according to the present invention, the camera 12, which captures medicines, is installed in the camera tube 11, which is formed in the shape of a tube, at one side thereof.

Also, a refraction plane 13 is formed in the camera tube 11 at a predetermined point thereof so that a predetermined angle is defined between one side and the other side of the camera tube 11.

In this embodiment of the present invention, the camera tube 11 is configured so that one side and the other side of the camera tube 11 are bent 90 degrees, i.e., in the shape of an 'L.'

A lens of the camera 12 installed at one side of the camera tube 11 recognizes an object located at the other side of the camera tube 11. To this end, the refraction plane 13 includes a reflection plate 13 for reflecting the other side of the camera tube 11.

That is, the reflection plate 13 reflects a medicine loading table 15 located at the other side of the camera tube 11.

The medicine loading table 15 is a space on which medicines, an image of which will be captured, are loaded.

Also, the illumination unit 17 is disposed over the medicine loading table 15.

Figure 3:
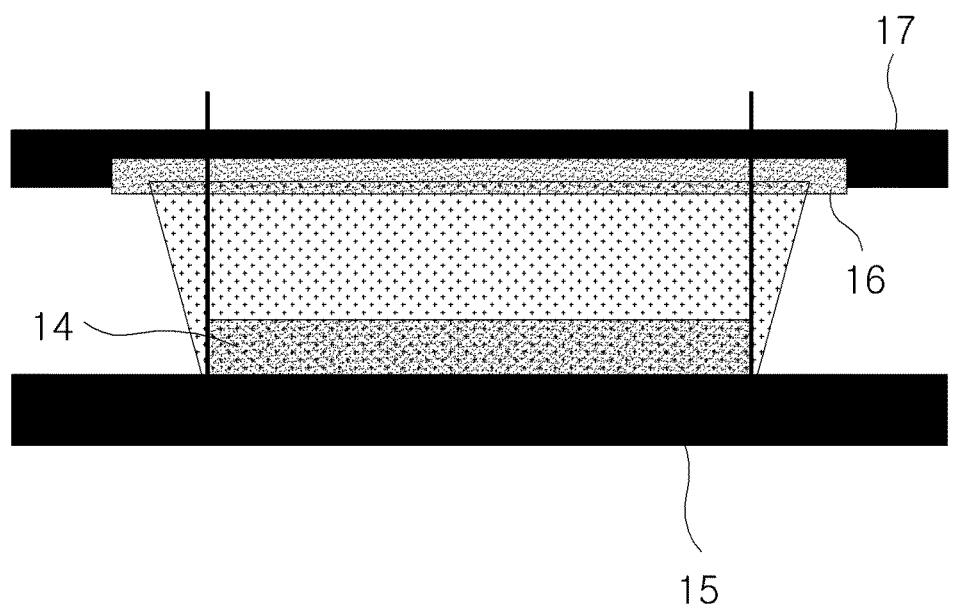
FIG. 3 is a schematic view illustrating the capturing construction of the medicine image capturing device according to the present invention.

As shown in FIG. 3, the illumination unit 17 drives an illumination device 16 located below the illumination unit 17 to adjust the brightness around medicines so that the shapes of the medicines loaded on the medicine loading table 1 can be clearly captured.

The medicine image capturing device 10 according to the present invention further includes a correction panel 14.

The correction panel 14 is exchangeable with the medicine loading table 15 of the camera tube 11. The correction panel 14 serves to test and correct camera setting values. Preferably, the correction panel 14 is formed of a transparent material. In this embodiment of the present invention, the correction panel 14 is formed of glass.

Figure 4:
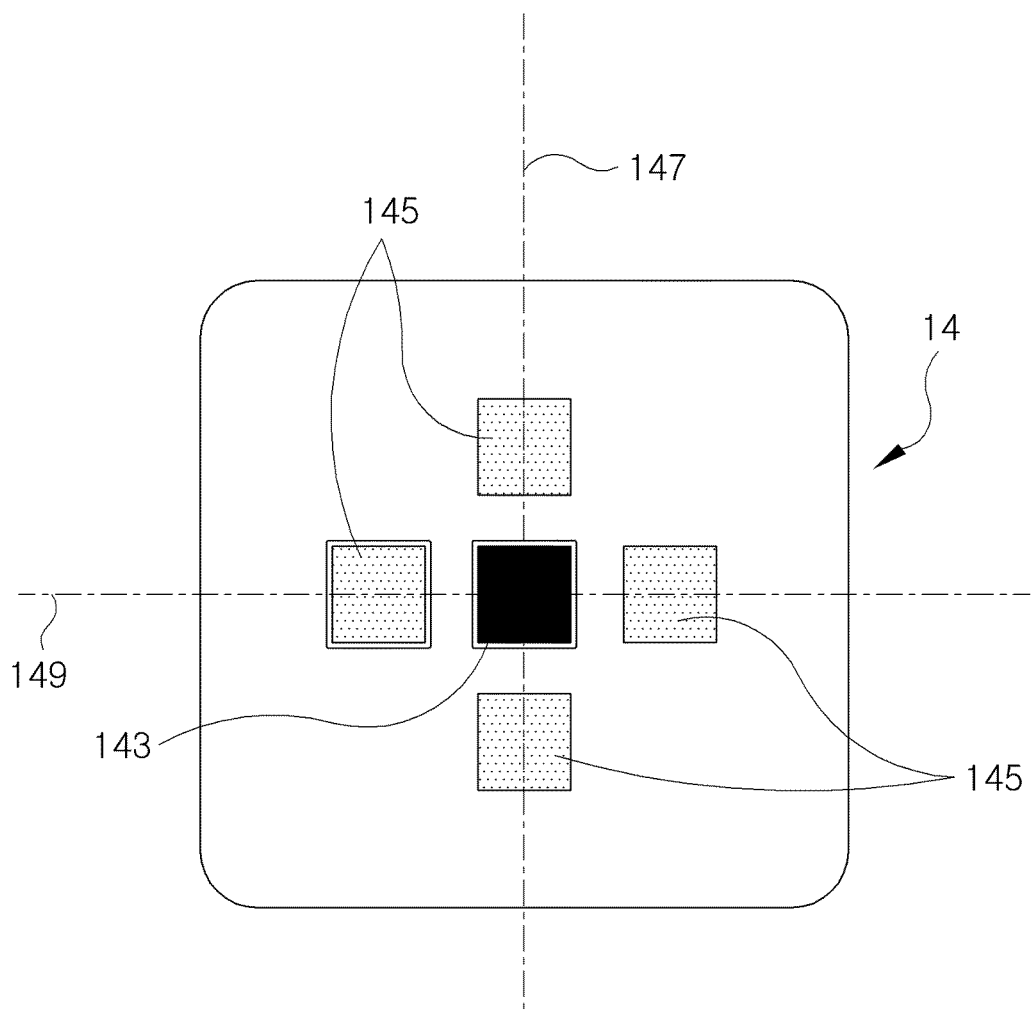
FIG. 4 is a view illustrating an embodiment of a correction panel of the medicine image capturing device according to the present invention.

Also, as shown in FIG. 4, the correction panel 14 includes at least one jig block so that the correction panel 14 can analyze camera setting elements through the jig block.

In this embodiment of the present invention, the correction panel 14 includes quadrangular jig blocks, which include a center jig block 143 and four auxiliary jig blocks 145 disposed around the center jig block 143.

The center jig block 143 is located at the center of the correction panel 14. During testing of the setting values of the camera 12, it is possible to test the position of the camera 12 through the center jig block 143.

The center of an image is defined as a point at which a horizontal center axis 149 and a vertical center axis 147 intersect. The camera is shifted so that the center coordinates of the center jig block 143 is located at the intersection point on an image of the correction panel 14 input to the camera 12 to find an appropriate position of the camera 12.

The auxiliary jig blocks 145 are located at the left side, the right side, the upper side, and the lower side of the center jig block 143. Intensity of the auxiliary jig blocks 145 is measured to reset an iris value of the camera lens.

The medicine image capturing device according to the present invention further includes a camera setting unit connected to the camera 12 for adjusting camera setting elements necessary to capture an image of medicines.

The camera setting unit serves to adjust and inspect at least one selected from a group consisting of a focus, an image center axis, an image scale, and intensity of the camera 12.

The focus of the camera lens is set using edge intensity distributions of the three jig blocks included in the horizontal center axis 149 on the basis of the horizontal center axis 149 of the correction panel 14 shown in FIG. 4.

The horizontal length and the vertical length of the center jig block 143 are measured to decide the image scale, i.e., the image size, of the medicines output from the camera. The image size of the medicines may be changed by adjusting the distance between the camera 12 and the medicine loading table 15.

Intensity of the auxiliary jig blocks 145 is measured to reset the iris value of the camera lens.

In the medicine image capturing device according to the present invention as described above, the camera is installed in the camera tube, which is formed in the shape of a tube. Consequently, it is possible to acquire images exhibiting uniform quality and to easily determine and reset camera setting values.

Hereinafter, a medicine management system using the medicine image capturing device as described above will be described in detail.

Figure 5:
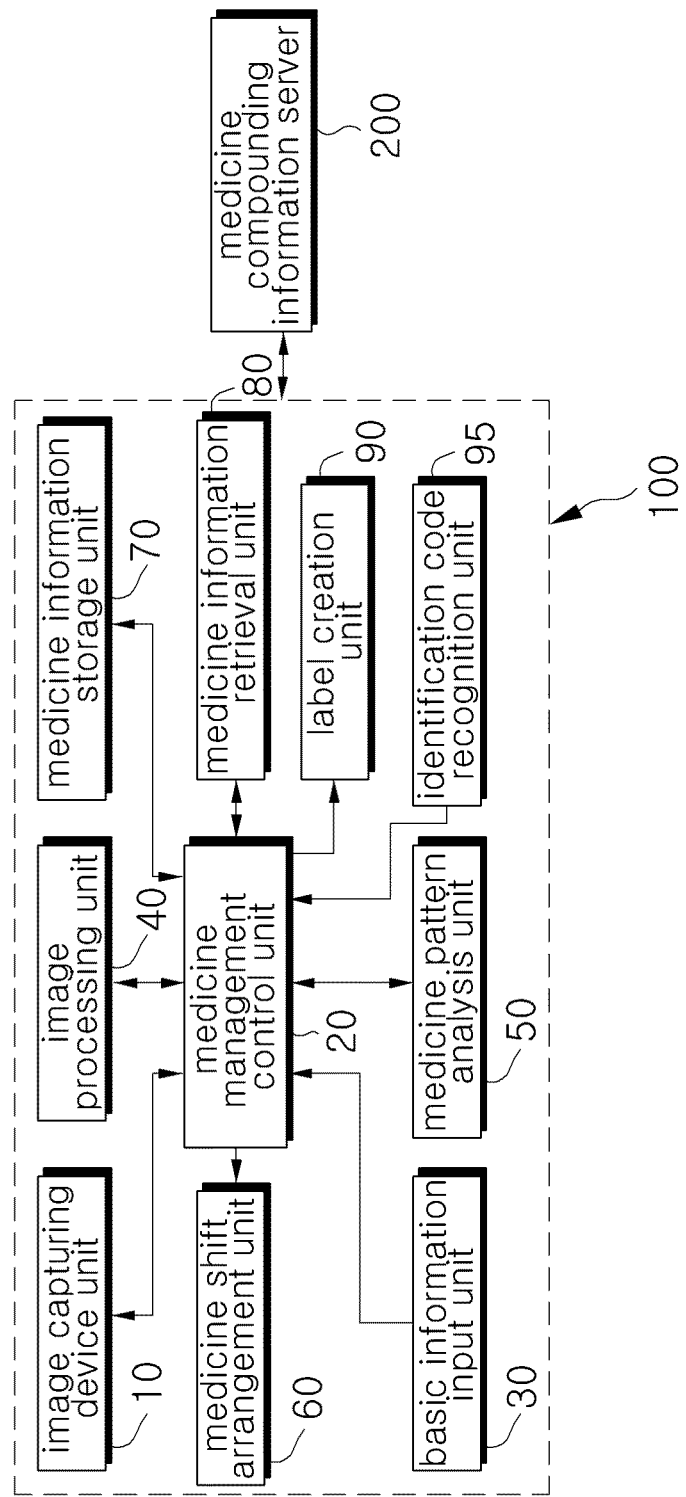
FIG. 5 is an overall construction view illustrating a medicine management system according to the present invention.

FIG. 5 is a construction view of a medicine management system according to the present invention. The medicine management system includes an image capturing device unit 10, a medicine management control unit 20, a medicine shift arrangement unit 60, a basic information input unit 30, an image processing unit 40, a medicine pattern analysis unit 50, a medicine information storage unit 70, a medicine information retrieval unit 80, a label creation unit 90, identification code recognition unit 95, and a medicine compounding information server 200.

The image capturing device unit 10 serves to capture an individual medicine or compound medicines. The image capturing device unit 10 includes the medicine image capturing device according to the present invention as previously described.

The medicine management control unit 20 collects and transmits the captured image of the medicines to the image processing unit 40. In addition, the medicine management control unit 20 controls an operation of calculating medicine pattern information, an operation of registering medicine information, and an operation of retrieving the medicine information based on the input medicine pattern information.

Also, the medicine management control unit 20 serves to control operation of the respective components to determine whether medicine compounding per package based on medicine compounding information provided from the medicine compounding information server 200 is abnormal.

The image processing unit 40 analyses and transmits the captured image of the individual medicine to the medicine management control unit 20. In addition, the image processing unit 40 serves to extract a medicine region from the medicine image to correct the position of the medicine and to extract a contour line of the medicine region through an image binarizing operation.

Also, the image processing unit 40 according to the present invention is connected to the medicine management control unit 20 for capturing an image per package of the compound medicines, with respect to which a barcode recognizing operation has been completed, for each single package of the compound medicines and for analyzing the captured image.

Figure 6:
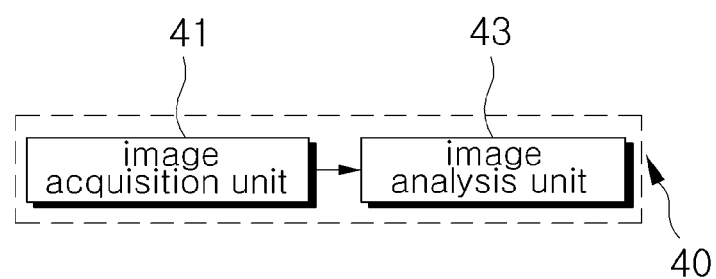
FIG. 6 is a detailed construction view illustrating an image processing unit of the medicine management system according to the present invention.

As shown in FIG. 6, the image processing unit 40 includes an image acquisition unit 41 and an image analysis unit 43.

The image acquisition unit 41 serves to collect the captured image frames per a predetermined reference interval. The collected image frames are transmitted to the image analysis unit 43.

The image analysis unit 43 serves to analyze the medicine image transmitted from the image acquisition unit 41 and to derive pattern information per medicine.

The pattern information per medicine includes size, quantity, shape, color, symbol mark, weight, and thickness of each medicine.

In this embodiment of the present invention, the image analysis unit 43 performs an image binarizing operation using a critical value.

In addition, the image analysis unit 43 extracts a circular image having a predetermined section from the center of each corner of the image, measures the area of the image and the angle of a separation line to distinguish joint corners of the medicines, and separates the medicines into independent regions.

The image analysis unit 43 transmits medicine pattern information based on the size and quantity of the medicines through the image of the independent regions of the medicines to the medicine management control unit 20, which determines whether the medicine pattern information coincide with the medicine compounding information.

The medicine pattern analysis unit 50 is connected to the medicine management control unit 20 for analyzing medicine patterns based on the medicine image analyzed by the image processing unit 40 and for calculating medicine pattern information.

The medicine pattern information according to present invention includes color, shape, marking, and external dimensions (thickness, length, width, area, etc.) of each of the medicines.

The color of the medicines may be obtained through a color image of the medicines. The shapes of the medicines may be determined based on the medicine image extracted in the form of a contour line. In addition, the external dimensions of the medicines may be calculated through the measurement of a length of the medicine image extracted in the form of the contour line on the basis of a reference point thereof.

Also, the medicine pattern analysis unit 50 according to the present invention is connected to the medicine management control unit 20 for storing the medicine pattern information through analysis of the image per medicine and for analyzing the medicine pattern of the medicine image captured by the image processing unit 40 to determine whether the compound medicines are normal.

Figure 7:
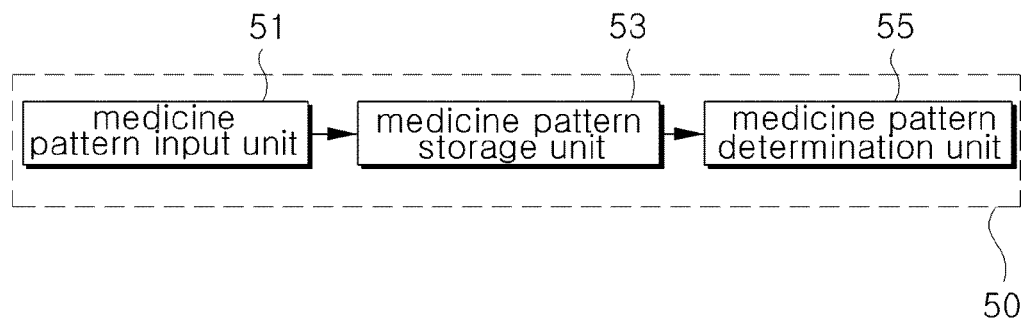
FIG. 7 is a detailed construction view illustrating a medicine pattern analysis unit of the medicine management system according to the present invention.
Figure 8:
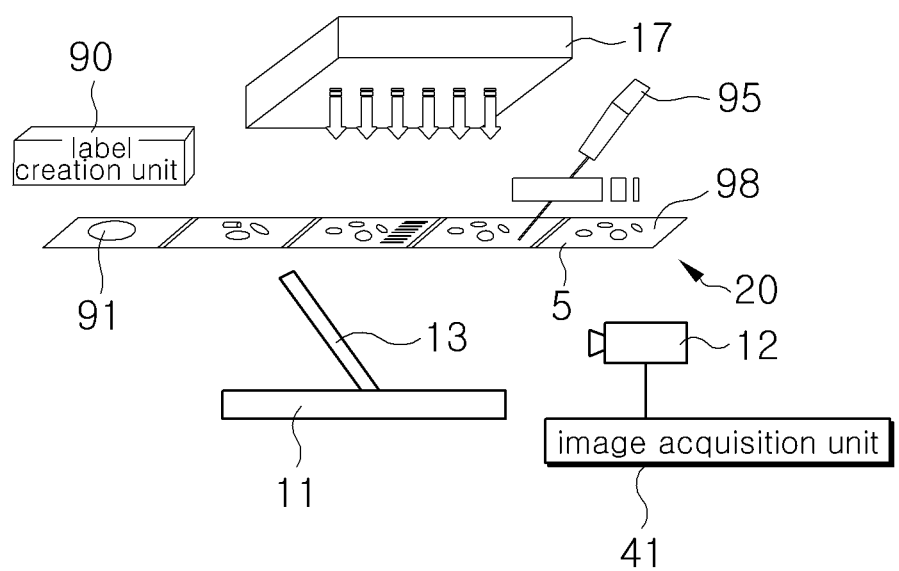
FIG. 8 is a conceptual view illustrating a compound medicine test in the medicine management system according to the present invention.

As shown in FIG. 7, the medicine pattern analysis unit 50 includes a medicine pattern input unit 51, a medicine pattern storage unit 53, and a medicine pattern determination unit 55.

The medicine pattern input unit 51 serves to input basic information of an individual medicine and medicine pattern information of an image obtained by capturing the external shapes of the medicines.

That is, basic information, such as a medicine name, a manufacturer name and usage, on each medicine is input through the medicine pattern input unit 51.

The medicine pattern storage unit 53 is connected to the medicine pattern input unit 51 and the medicine pattern determination unit 55 for storing the basic information of the individual medicine and for storing pattern information of the individual medicine analyzed by the medicine pattern determination unit 55.

The medicine pattern determination unit 55 is connected to the medicine management control unit 20 for comparing the medicine pattern information of the medicine image received from the medicine management control unit 20 with the medicine pattern information stored in the medicine pattern storage unit 53 to determine whether the medicine pattern information received from the medicine management control unit 20 coincides with the medicine pattern information stored in the medicine pattern storage unit 53.

In this embodiment of the present invention, it is determined whether the medicine pattern information coincides with histogram information based on the external shapes of the medicines to determine whether compound medicines are defective. The medicine pattern information further includes additional analysis conditions, such as color, symbol mark, weight, and thickness, of medicines, thereby improving accuracy in testing of the compound medicines.

The medicine pattern information calculated by the medicine pattern analysis unit 50 is transmitted to the medicine management control unit 20. Also, the medicine pattern information is registered in the medicine information storage unit 70.

In this embodiment of the present invention, the basic information of the medicines input through the basic information input unit 30 is also stored during the registration of the medicine pattern information.

The basic medicine information according to the present invention further includes a medicine name, a medicine manufacturer name, and the available period in addition to the medicine pattern information.

Also, the medicine image captured by the image capturing device unit 10 and the medicine image information analyzed by the image processing unit 40 are stored in the medicine information storage unit 70.

As described above, the medicine information of the present invention includes the basic medicine information, the medicine pattern information, and the medicine image information. The more medicine information elements there are, the higher retrieval accuracy is.

The medicine shift arrangement unit 60 serves to change capturing directions or capturing positions of medicines to be captured during the registration of individual medicine information.

That is, the capturing direction of the medicines is changed to capture the medicines in various directions, i.e., at the front, at the rear, and at the side thereof.

In this way, the medicines are captured in various directions, and then the analyzed medicine pattern information is managed. Consequently, it is possible to derive accurate medicine retrieval results through comparison of the pattern elements between medicines having similar external shapes.

Also, the medicine shift arrangement unit 60 according to the present invention serves to automatically shift packaged compound medicines such that a barcode recognizing operation per medicine package of the identification code recognition unit 95, an image capturing operation of the image processing unit 40, and a label attaching operation of the label creation unit 90 can be easily performed during testing of the compound medicines.

It is possible to sequentially perform the test processes and thus reduce time necessary to test the compound medicines by the provision of the medicine shift arrangement unit 60.

Also, the medicine shift arrangement unit 60 according to the present invention preferably includes a rearrangement unit.

The rearrangement unit serves to shake the medicines from side to side or up and down to rearrange the medicines when the captured state of the medicines in the image collected by the image acquisition unit 41 is not good.

That is, it is possible to recapture the medicines during shift of the medicine image with respect to which an analysis operation is difficult by the provision of the rearrangement unit, thereby reducing image analysis time.

The medicine information retrieval unit 80 serves to retrieve the basic medicine information stored in the medicine information storage unit 70 using the image information and the medicine pattern information calculated by the medicine pattern analysis unit 50.

The label creation unit 90 serves to create a normal state indicating label or an abnormal state indicating label per medicine package depending upon the determination of the medicine pattern analysis unit 50 as to whether the medicines are defective and to attach the labels to medicine packaging paper.

It is possible to easily identify compound medicines which have been determined to be defective through such label creation and attachment.

The identification code recognition unit 95 is connected to the medicine management control unit 20. During storage of an individually packaged medicine, the identification code recognition unit 95 recognizes identification code information formed on each sheet of the medicine packaging paper and transmits the recognized barcode information to the medicine management control unit 20.

In this embodiment of the present invention, the identification code includes a barcode 98. Medicine compounding information is received from the medicine compounding information server 200 using the information of the barcode 98 received from the identification code recognition unit 95.

The medicine compounding information server 200 may be a server installed in a hospital or a pharmacy for managing medicine compounding information and an identification code formed per medicine package.

The medicine compounding information includes information related to medicine compounding, such as a patient, a person in charge, a prescription date, prescription contents, a dosage period and the quantity of compound medicines.

Also, the identification code enables the medicine compounding information of each medicine to be easily retrieved. In this embodiment of the present invention, the identification code includes a barcode. Alternatively, the identification code may include a radio frequency identification (RFID) tag or a series of numbers or letters.

As described above, the medicine management system according to the present invention analyzes and manages medicine pattern information to provide a management standard on medicine information. Also, the medicine management system according to the present invention analyzes medicine pattern information using a medicine image and retrieves the stored medicine information. Consequently, it is possible for the medicine management system according to the present invention to improve efficiency and accuracy of medicine retrieval and management.

Hereinafter, a medicine management method using the medicine image capturing device according to the present invention will be described in detail.

Figure 9:
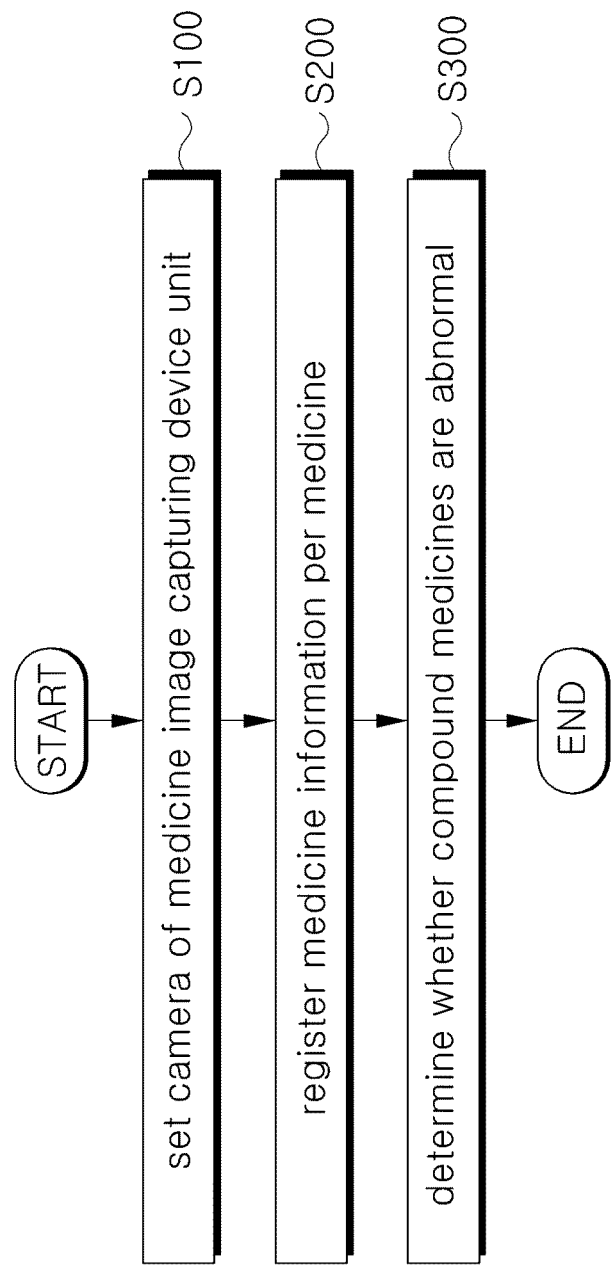
FIG. 9 is an overall flow chart illustrating a medicine management method according to the present invention.

FIG. 9 is an overall flow chart illustrating a medicine management method according to the present invention. As shown in FIG. 9, a step of setting the camera 12 of the image capturing device unit 10 is performed (S100).

Figure 10:
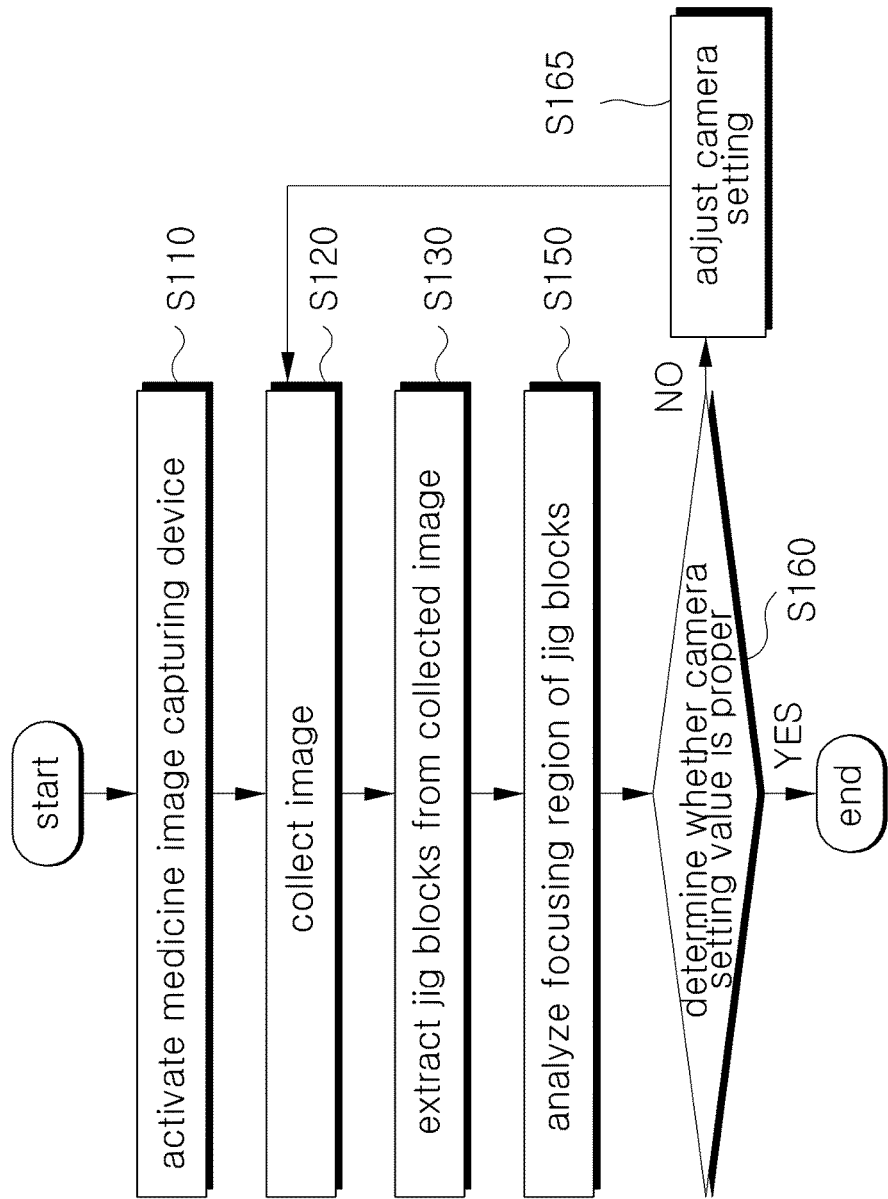
FIG. 10 is a detailed flow chart illustrating Step S100 of the medicine management method according to the present invention.

FIG. 10 is a detailed flow chart illustrating Step S100 of the medicine management method according to the present invention. First, a step of activating the medicine image capturing device is performed (S110).

Step S110 is a step of setting the respective components of the medicine image capturing device. Step S110 includes a jig setting loading step, a camera setting step, an illumination setting step, and a mechanism setting step.

Subsequently, a step of acquiring a captured image is performed (S120).

Step S120 is a step of capturing an image of the correction panel loaded on the medicine loading table 15 located at the other side of the camera tube 11 using the camera 12 and collecting the image using the image acquisition unit 41.

Subsequently, a step of extracting jig blocks from the collected image is performed (S130).

Step S130 is a step of extracting the jig blocks formed at the correction panel 14. Step S130 may include a step of extracting the center jig block 143 and a step of extracting the auxiliary jig blocks 145.

Figure 11:
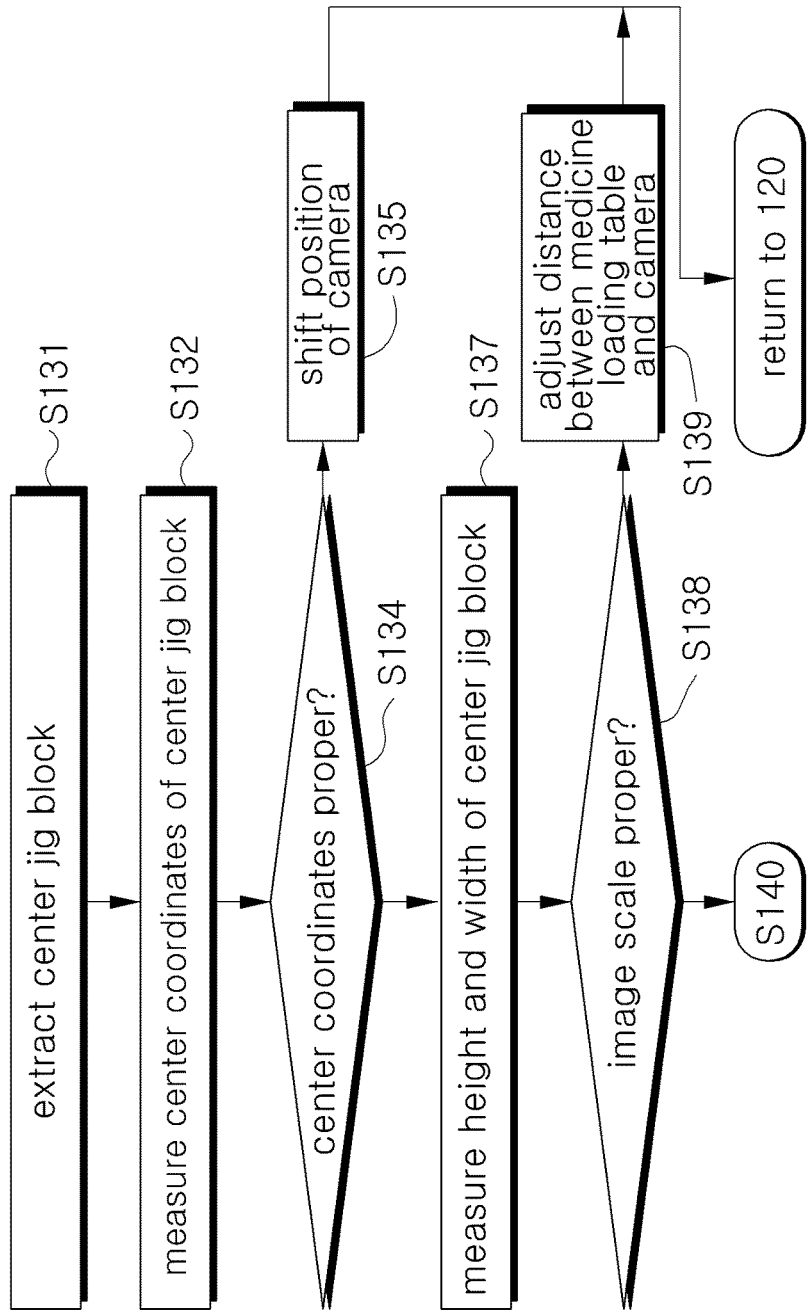
FIGS. 11 and 14 are detailed flow charts illustrating Step S130 and Step S140 of the medicine management method according to the present invention.

FIG. 11 is a detailed flow chart illustrating the step of extracting the center jig block 143. First, a step of extracting a region of the center jig block 143 is preformed (S131).

Subsequently, a step of measuring center coordinates of the center jig block 143 is preformed (S132).

Figure 12:
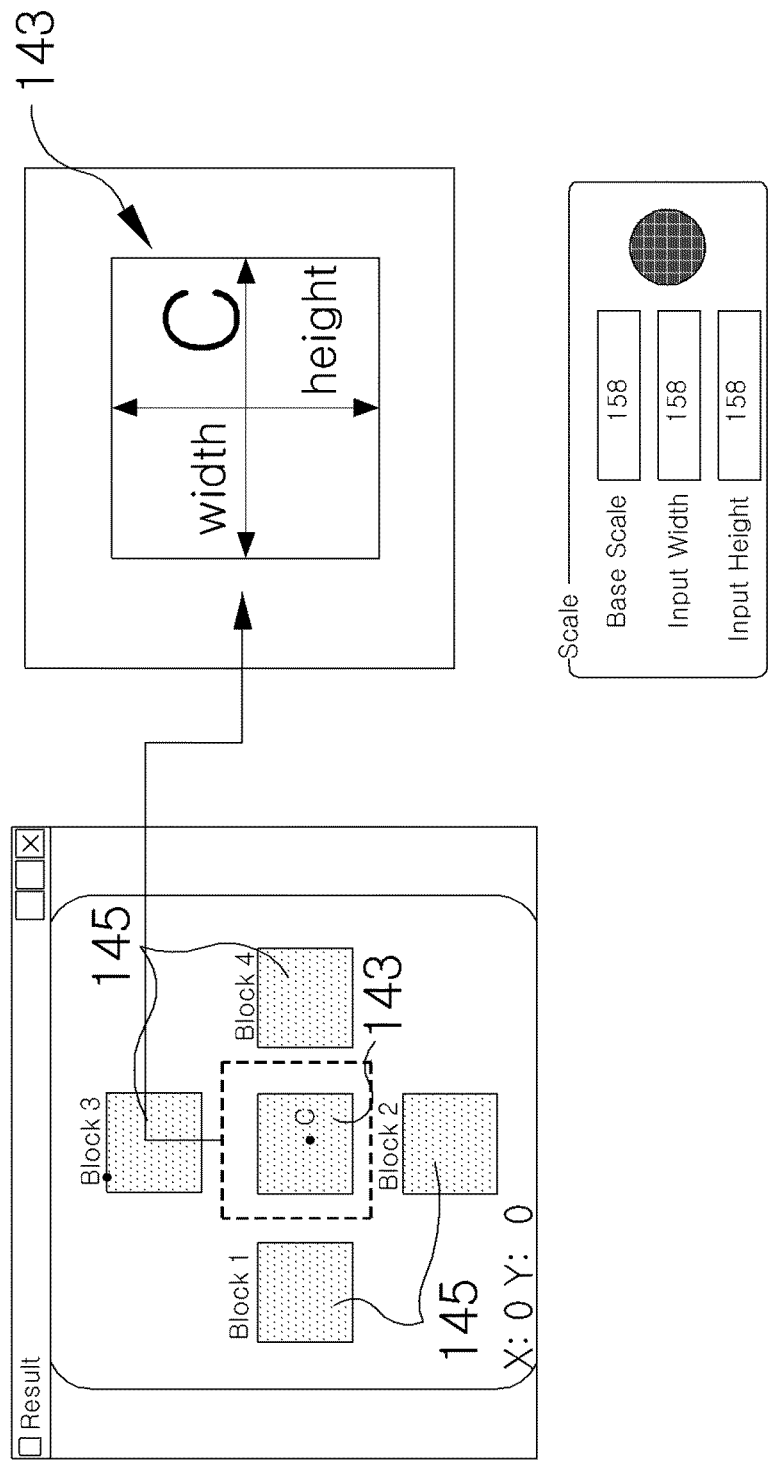

Step S132 is a step of measuring center coordinates C of the center jig block 143 as shown in FIG. 12.

Subsequently, a step of comparing the measured center coordinates of the center jig block 143 with predetermined center coordinates C to determine whether the measured center coordinates of the center jig block 143 coincides with the predetermined center coordinates C is performed (S134). Upon determining that the measured center coordinates of the center jig block 143 deviates from the predetermined center coordinates C, a step of shifting the position of the camera is performed (S135) to correct the center coordinates C.

Subsequently, a step of measuring the height and width of the center jig block 143 is performed (S137).

Figure 13:
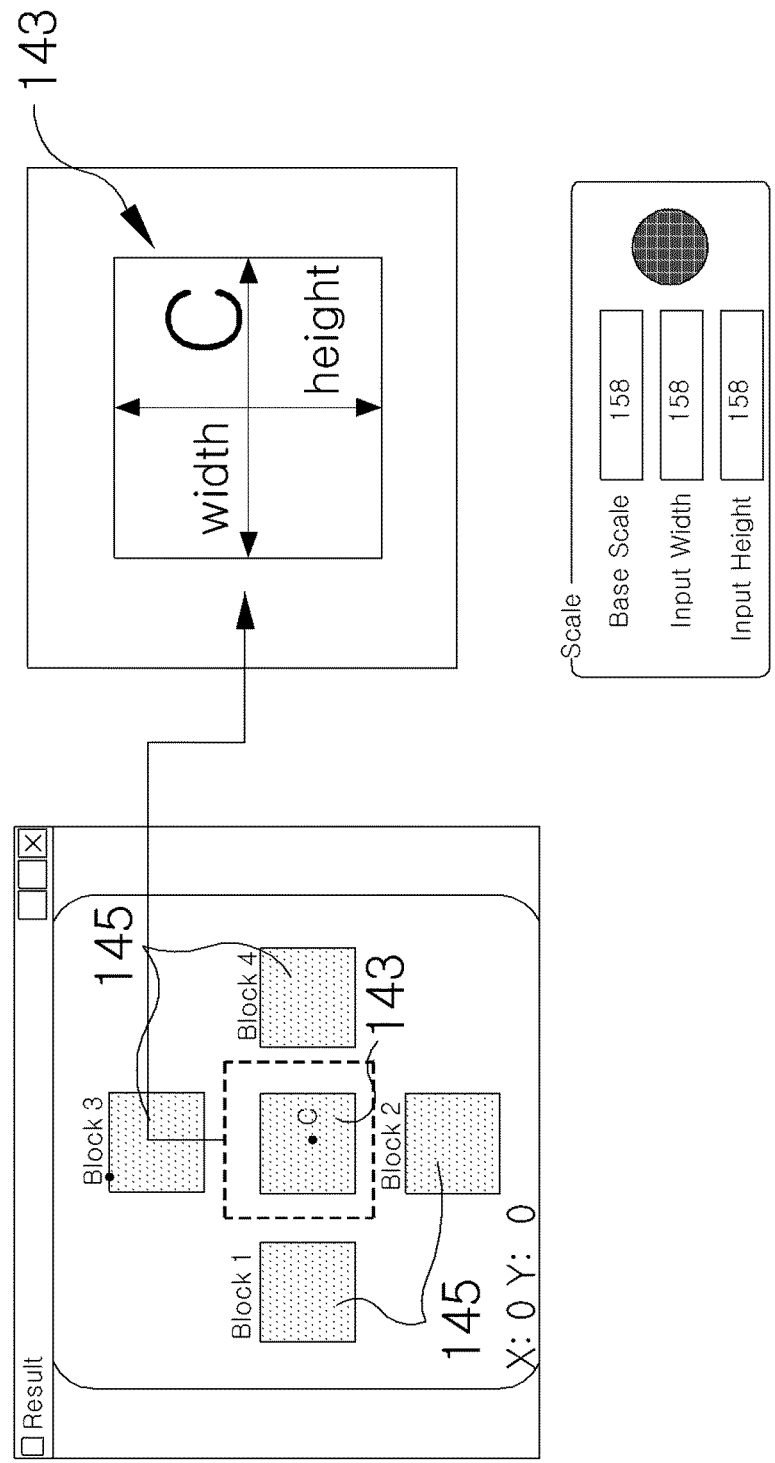

Step S137 is a step of analyzing the center jig block 143 to measure the width and height of the center jig block 143 as shown in FIG. 13. An image scale is extracted based on the width and height of the center jig block 143.

It is determined whether the image scale extracted at Step S137 is proper (S138). Upon determining that the extracted image scale is not proper, a step of adjusting the distance between the medicine loading table 15 and the camera 12 (S139) to correct the image scale is preferably performed.

Figure 14:
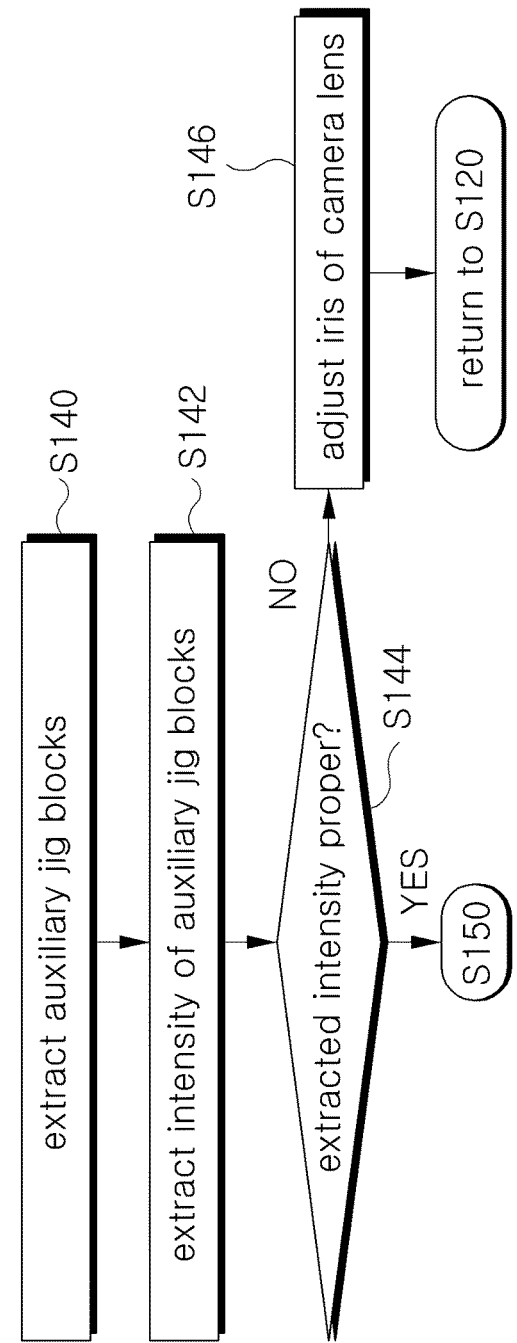

FIG. 14 is a detailed flow chart illustrating the step of extracting the auxiliary jig blocks 145. First, a step of extracting a region of the auxiliary jig blocks 145 is preformed (S140).

Subsequently, a step of extracting the intensity of the auxiliary jig blocks 145 is performed (S142).

Figure 15:
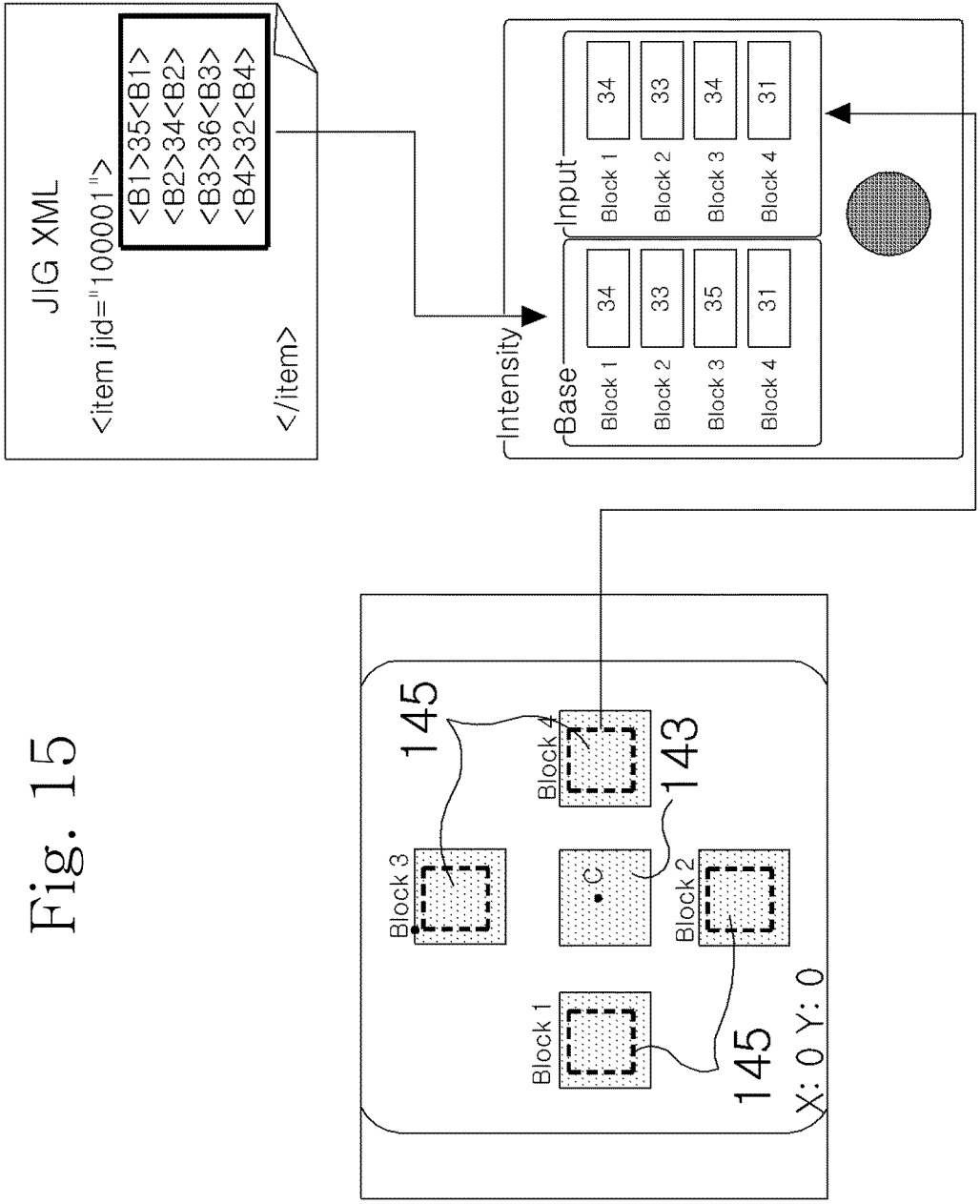

At Step S142, the intensity of the four auxiliary jig blocks 145 excluding the center jig block 143 is extracted, as shown in FIG. 15.

It is determined whether the intensity of the auxiliary jig blocks 145 extracted at Step S142 is proper (S144). Upon determining that the extracted intensity of the auxiliary jig blocks 145 is not proper, a step of adjusting the iris of the camera lens (S146) to correct the intensity of the image is preferably performed.

Subsequently, a step of analyzing a focusing region 146 of the jig blocks is performed (S150).

Step S150 is a step of analyzing an edge intensity distribution of the input image of the correction panel 14 to determine whether the focus is correct, as shown in FIG. 16. In this embodiment of the present invention, the focusing region 146 is designated as a region including the center jig block 143 and portions of the auxiliary jig blocks 145 located at the left and right sides of the center jig block 143. Alternatively, the focusing region 146 may be arbitrarily designated.

The edge component of the focusing region 146 of the jig blocks may be analyzed using a method of extracting an intensity gradient.

Subsequently, a step of determining whether the camera setting value is proper is performed (S160).

Figure 17:
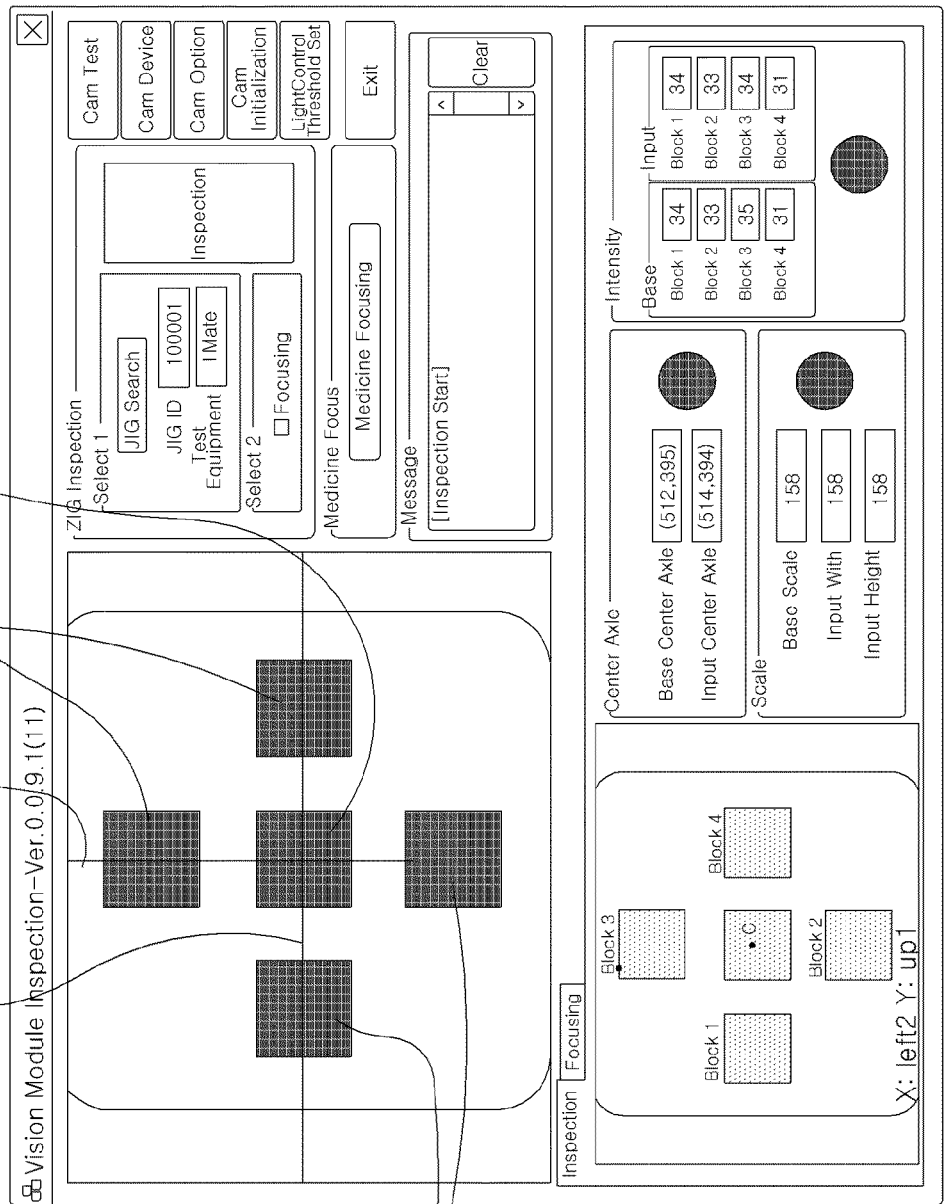

Step S160 is a step of determining whether the camera setting value is proper based on the image analysis elements measured at Step S130 and Step S150, as shown in FIG. 17.

Upon determining at Step S160 that the camera setting value is not proper, the camera setting is readjusted (S165), the procedure returns to Step 120, and subsequent processes are performed again.

As described above, it is possible to synchronize the camera setting of the medicine image of the medicine information management system and an automatic compound medicine test system through Step S100 of the present invention, thereby improving efficiency and accuracy of medicine image processing.

Subsequently, a step of registering and retrieving medicine information of an individual medicine is performed (S200).

Figure 18:
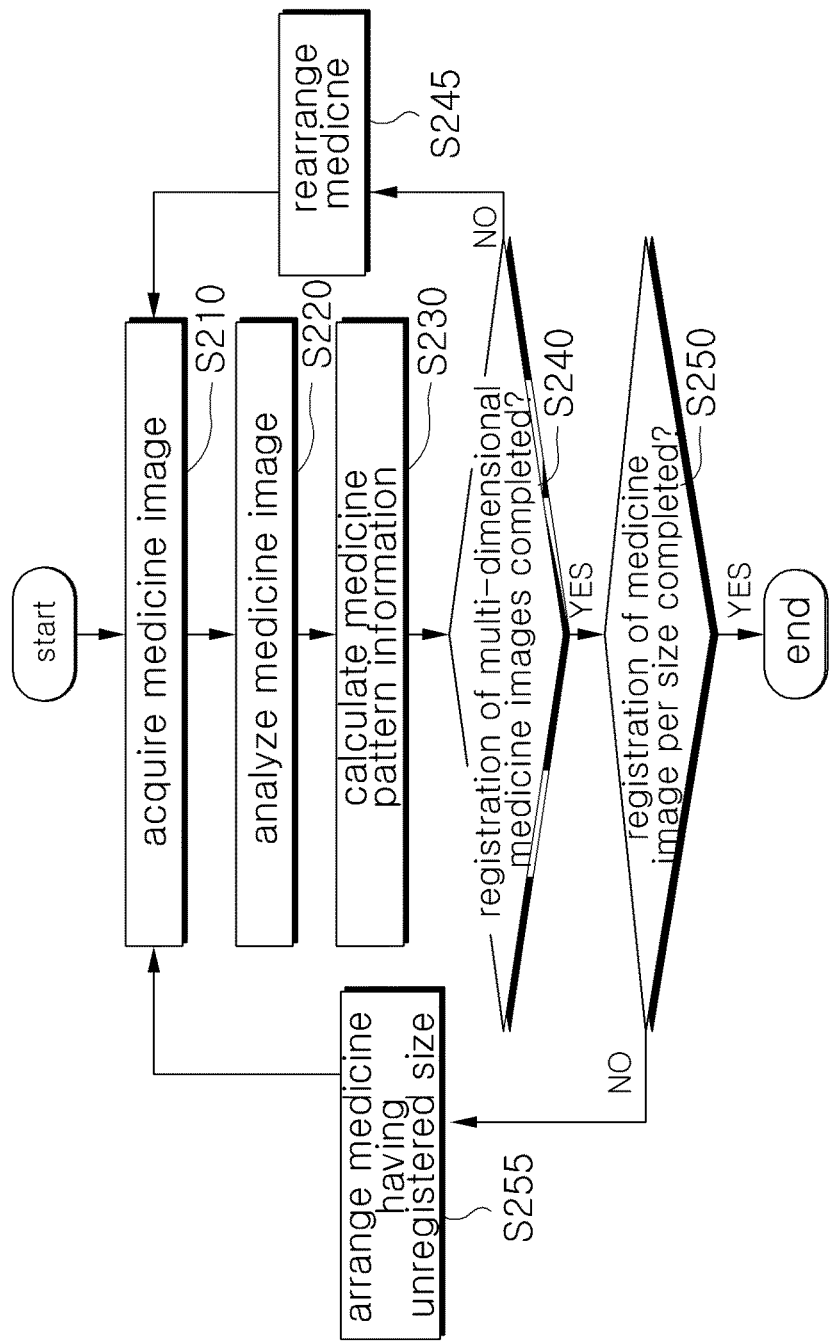
FIG. 18 is a detailed flow chart illustrating Step S200 of the medicine management method according to the present invention.

FIG. 18 is a detailed flow chart of Step S200. First, a step of acquiring a medicine image is performed (S210).

Figure 19:
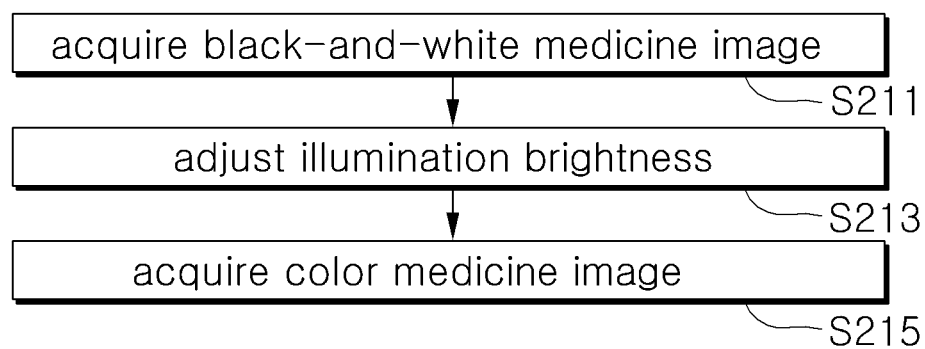
FIGS. 19, 20 and 22 are detailed flow charts illustrating Step S210, Step S220 and Step S230 of the medicine management method according to the present invention.

Step S210 is a step of capturing medicines to be registered using the image capturing device unit 10. FIG. 19 is a detailed flow chart of Step S210.

First, a step of acquiring a black-and-white image of an individual medicine using the image acquisition unit 41 is performed (S211).

Step S211 is a step of capturing an image in a state in which the illumination unit 16 is adjusted to be bright.

Subsequently, a step of adjusting illumination brightness of the illumination unit 16 is performed (S213).

Subsequently, a step of acquiring a color image of the medicines is performed (S215).

That is, it is possible to acquire both the color image and the black-and-white image of the medicines using the signal image capturing device unit 10 by adjusting the brightness of the illumination unit 16.

Subsequently, a step of analyzing the captured image of the medicines is performed (S220).

Figure 20:
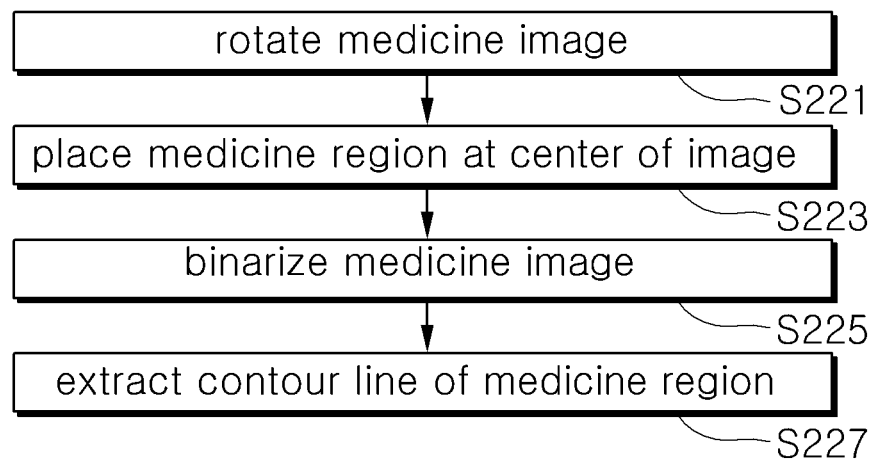

Step S220 is a step of analyzing the image captured by the image capturing device unit 10 through the image analysis unit 43. FIG. 20 is a detailed flow chart of Step S220.

First, a step of rotating the captured image of the medicines is performed (S221).

Step S221 is a step of rotating a rotation angle of the image such that the marking of each of the captured medicines is directed in the forward direction. The captured image of the medicines may be manually or automatically rotated according to setting.

Subsequently, a step of detecting a medicine region and placing the medicine region at the center of the image is performed (S223).

Step S221 and Step S223 are performed to improve convenience of a medicine image analyzing operation and to place the medicine region at the same position of the image during retrieval of medicine information.

Subsequently, a step of binarizing the medicine image is performed (S225).

Step S225 is a step of binarizing the black-and-white image of the medicines using a critical value. The critical value is a reference pixel value for binarizing the black-and-white image.

Figure 21:
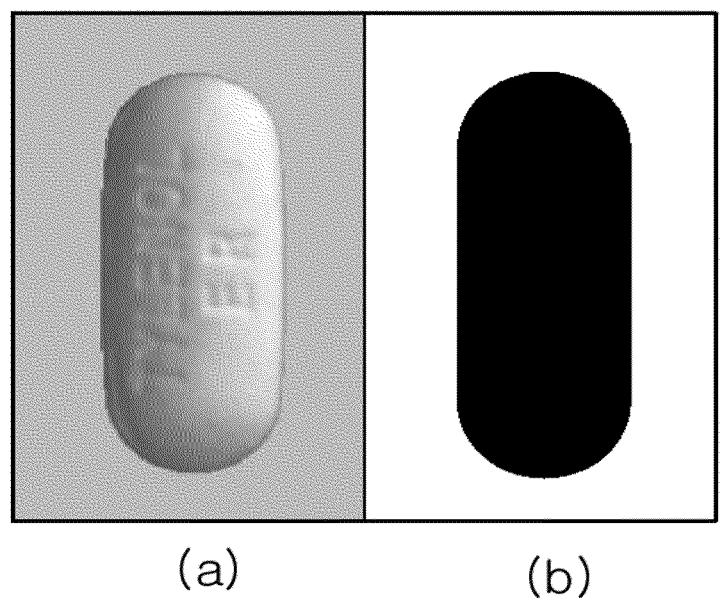
FIGS. 21, 23 and 24 to 26 are views illustrating an embodiment of Step S210 to Step S230 of the medicine management method according to the present invention.

FIG. 21 is a view illustrating an embodiment of a color medicine image (a) and a binarized image (b) obtained at Step S220.

Figure 25:
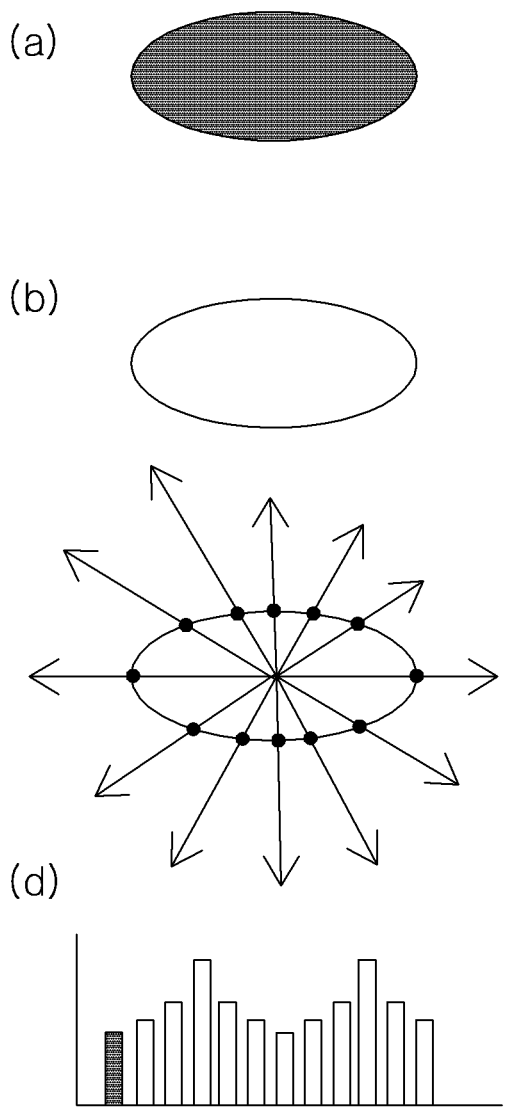

Also, FIG. 25(*a*) is a view illustrating an embodiment of Step S225.

Subsequently, a step of extracting a contour line of a medicine region is performed (S227).

Step S227 is a step of extracting an independent medicine region from the medicine image and extracting a contour line of the medicine region.

FIGS. 25(*b*) and 25(*c*) are views illustrating an embodiment of Step S227.

Subsequently, a step of calculating medicine pattern information using the medicine pattern analysis unit 50 is performed (S230).

Figure 22:
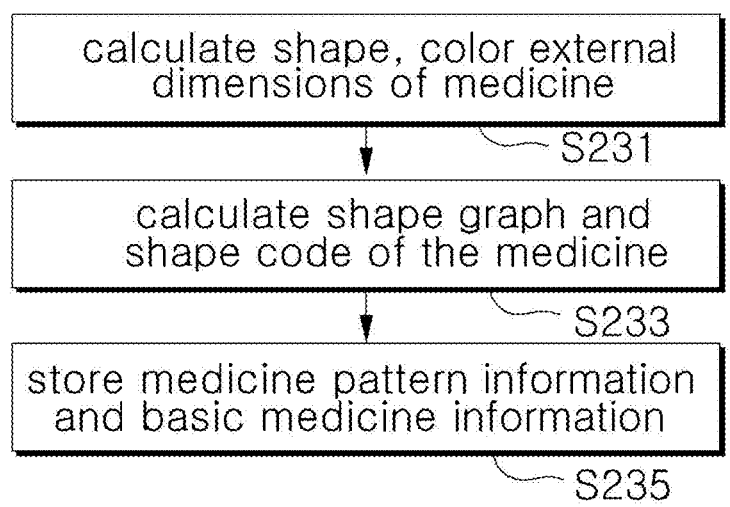

Step S230 is a step of calculating various kinds of pattern information (color, shape, marking, external dimensions, etc.) of each of the medicines based on the image analyzed at Step S220. FIG. 22 is a detailed flow chart of Step S230.

First, a step of calculating the color, shape, marking, and external dimensions of each of the medicines is performed (S231).

At Step S231, color information of the medicines is calculated based on the color image of the medicines, and a marking pattern of the medicines is calculated. Subsequently, the shapes and external dimensions of the medicines are calculated based on the image extracted in the form of a contour line. As shown in FIG. 25(*c*), the distance from the center point of each medicine to the contour line of the medicine is measured to calculate the external dimensions, such as thickness, length, width and area, of the medicine. Also, the shape of each medicine is calculated based on the form of the contour line.

Subsequently, a step of calculating a shape graph and shape code of the medicines is performed (S233).

Figure 26:
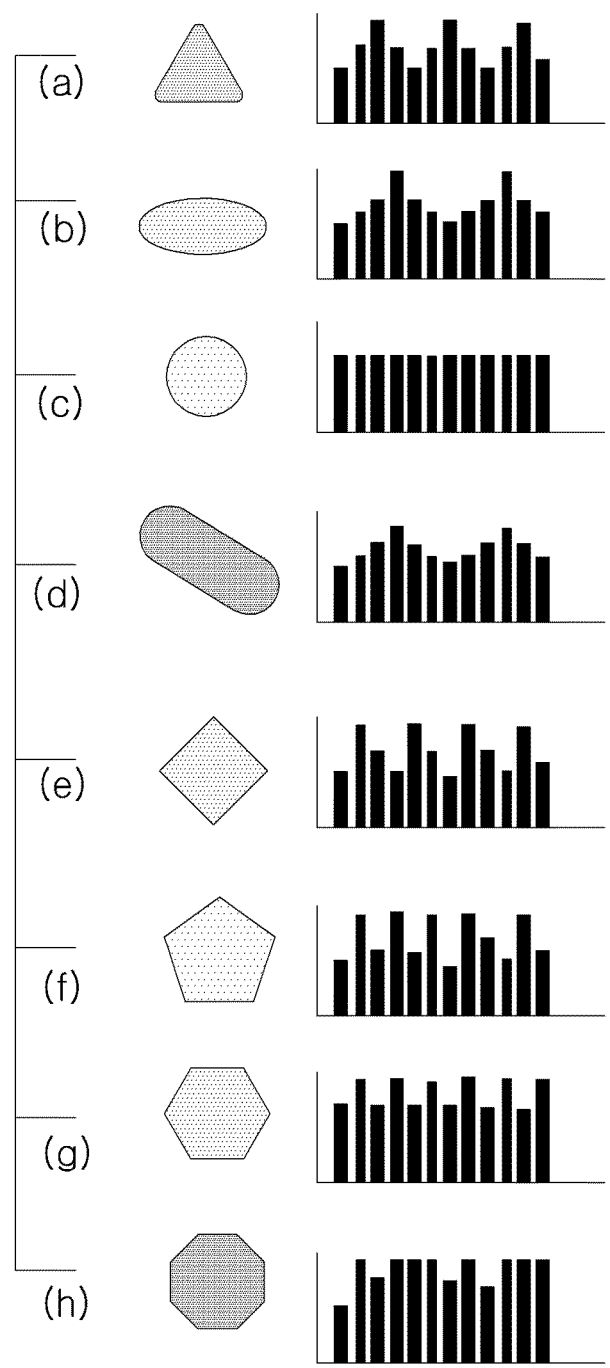

Step S233 is a step of calculating the medicine pattern information calculated at Step S231 in the form of a graph, a diagram, a code, etc. FIG. 25(*d*) is a view illustrating an embodiment of calculating a histogram according to the external dimensions of the medicines, and FIG. 26 is a view illustrating histograms based on shapes of medicines.

Subsequently, a step of storing the calculated medicine pattern information and basic medicine information is performed (S235).

Step S235 includes a step of inputting basic medicine information, such as a medicine name, a medicine manufacturer name, and the available period, through the basic information input unit 30.

Also, it is preferable to store the medicine image captured by the image capturing device unit 10 and the medicine image analyzed by the image processing unit 40.

As a result, the medicine image information, the basic medicine information and the medicine pattern information are all stored in the medicine information storage unit 70.

Subsequently, a step of determining whether registration of multi-dimensional medicine images has been completed is performed (S240).

Figure 23:
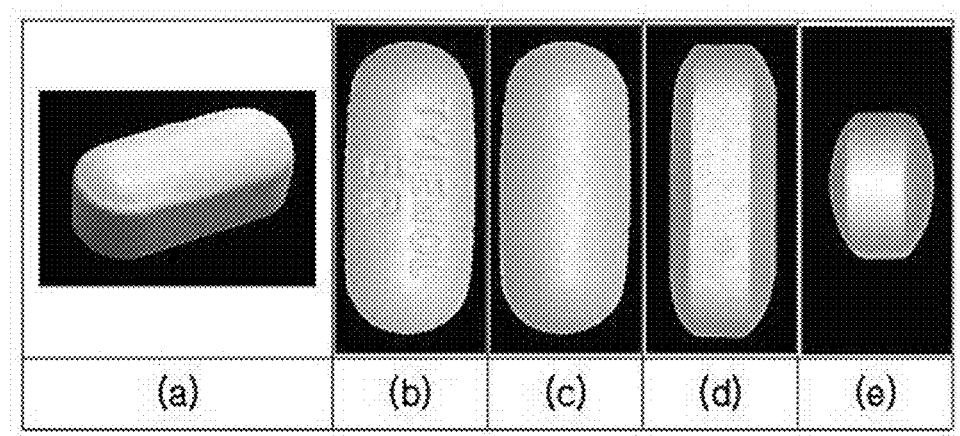
Figure 24:
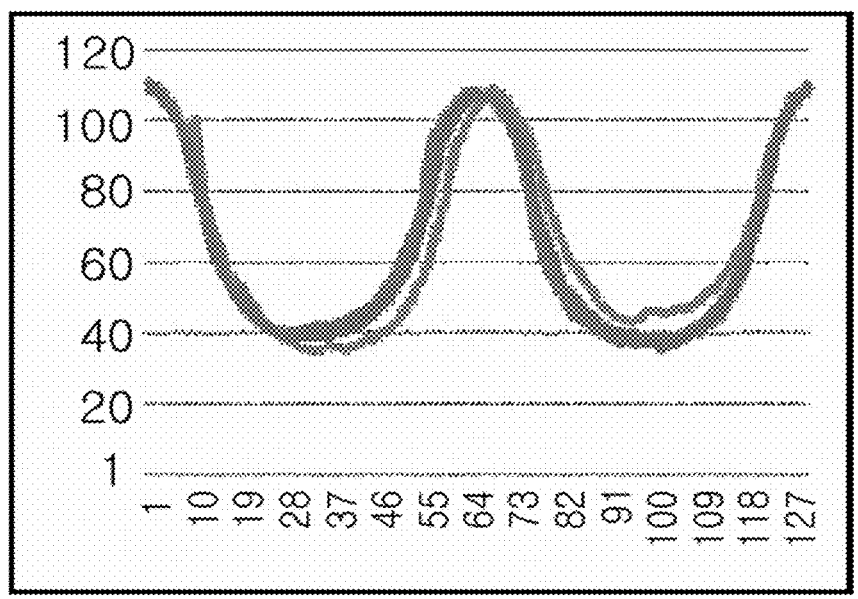

FIG. 23 is a view illustrating examples of captured images at the front (b), at the rear (c), at the side (d) and at the top (e) of a medicine based on the shape of the medicine (a). Preferably, a medicine is captured in various directions to detect various shapes of the medicine at the respective directions, thereby accurately identifying the medicine.

Step S240 is a step of determining whether the images of the medicine captured in various directions have been analyzed. Upon completion of registration, a step of determining whether registration of the medicine image per size has been completed is performed (S250).

Upon determining at Step S240 that all of the multi-dimensional medicine images have not been registered, a step of rearranging the capturing direction of the medicine is performed (S245), and the procedure returns to Step S210.

Step S250 is a step of determining whether medicine image analysis based on a cutting size (for example, ½, ⅓, ¼ . . . ) has been completed. Upon completion of the registration, the procedure is ended.

Upon determining at Step S250 that the image of the medicine per cutting size has not been registered, a step of arranging medicines having unregistered cutting sizes is performed (S255), and the procedure returns to Step S210.

In this way, it is possible to analyze the medicine images captured in various directions, not in a single direction, through Step S200 of the present invention and to calculate medicine pattern information, thereby variously and accurately analyzing the medicine pattern information.

Subsequently, a step of determining whether the compound medicines are abnormal is performed (S300).

Figure 27:
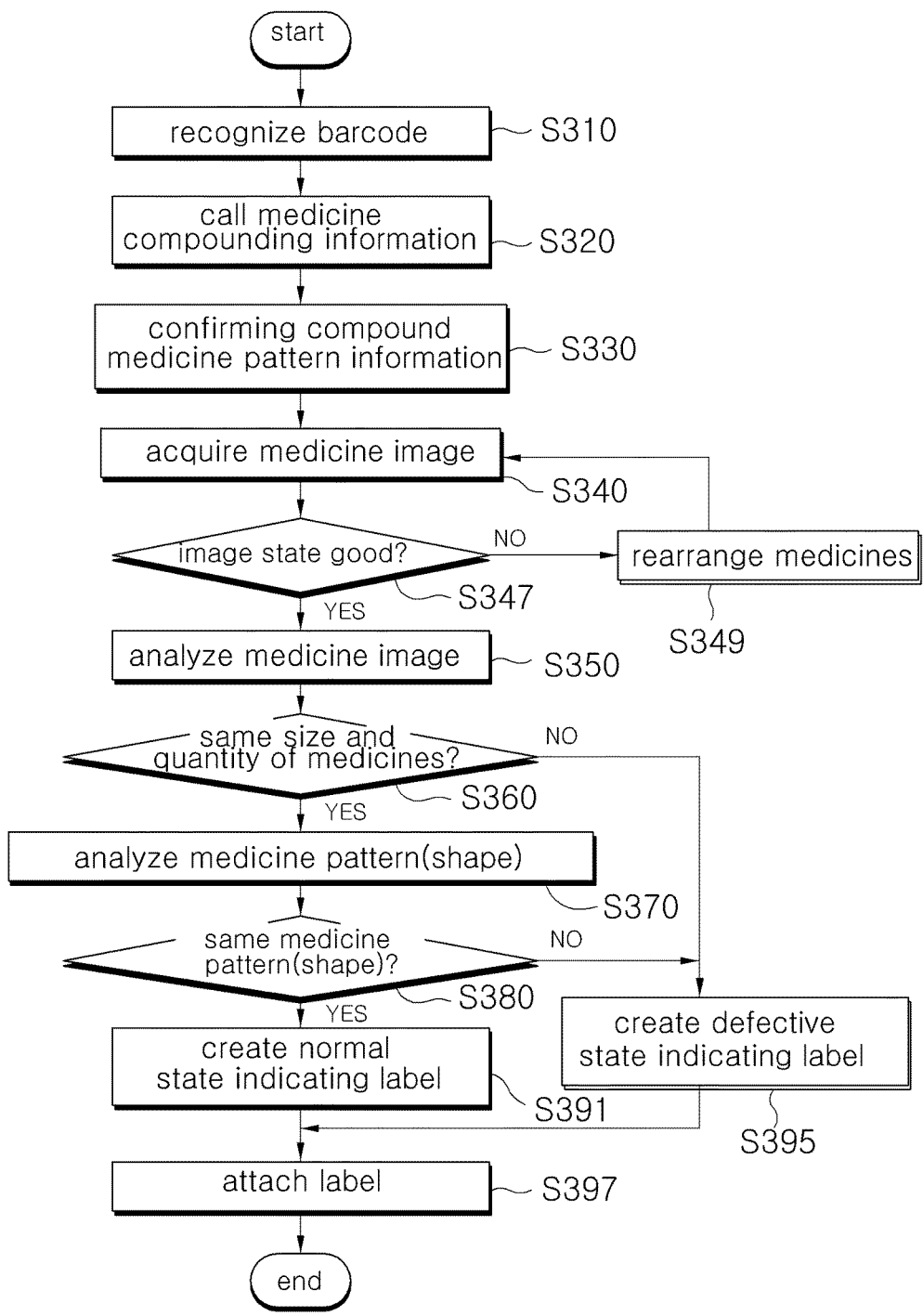
FIG. 27 is a detailed flow chart illustrating Step S300 of the medicine management method according to the present invention.

FIG. 27 is a detailed flow chart of Step S300 of the present invention. A step of recognizing an identification code per package of the medicines is performed (S310).

In this embodiment of the present invention, the identification code includes a barcode. At Step S310, therefore, the barcode 98 formed on the medicine packaging paper is recognized using the identification code recognition unit 95.

Subsequently, a medicine compounding information calling step of retrieving medicine compounding information from the medicine compounding information server 200 using the recognized barcode information is performed (S320).

Step S320 is a step of calling information related to a medicine prescription of a hospital or a pharmacy, i.e., information such as a medicine name and quantity of a medicine. It is possible to reduce time necessary to retrieve the medicine compounding information by the provision of the barcode information.

Subsequently, a step of confirming the medicine compounding information received from medicine compounding information server 200 and confirming the medicine pattern information stored in the medicine pattern analysis unit based on the medicine compounding information is performed (S330).

The medicine pattern information includes size, shape, color, symbol mark, weight, and thickness of the medicines stored in the medicine information storage unit 70.

Subsequently, an image acquisition step of capturing an image per package of the compound medicines and collecting the captured image using the image processing unit 40 is performed (S340).

Figure 28:
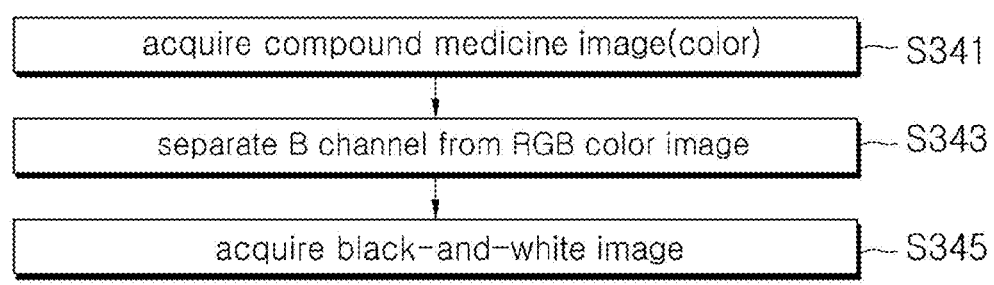
FIGS. 28, 30 and 32 are detailed flow charts illustrating Step S340, Step S350 and Step S370 of the medicine management method according to the present invention.

FIG. 28 is a detailed flow chart of Step S340. First, a step of capturing a red, green and blue (RGB) color image of compound medicines using the camera 12, as shown in FIG. 29(b), and acquiring an image frame through the image acquisition unit 41 is performed (S341).

Subsequently, a step of separating a B channel from the RGB color image is performed (S343).

Figure 29:
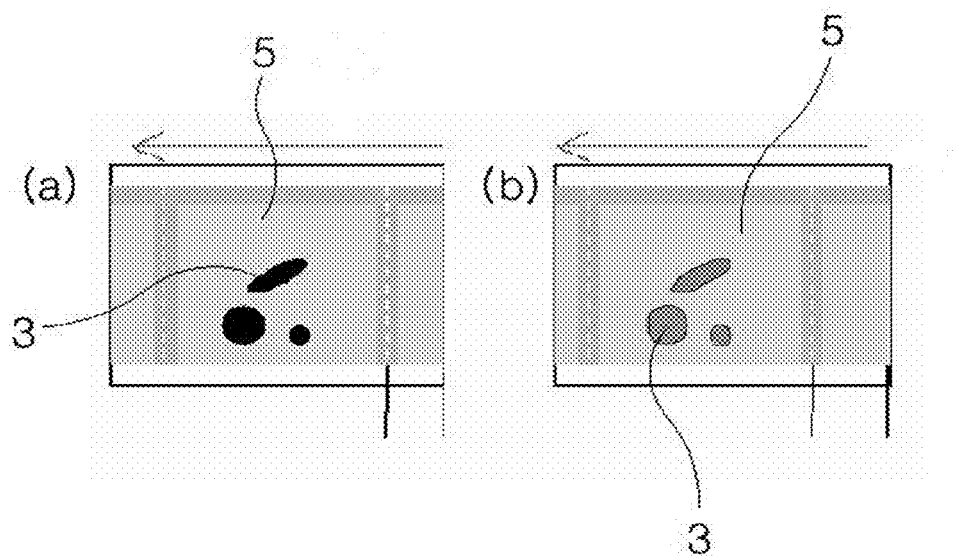

Subsequently, a step of acquiring a black-and-white image of the compound medicines as shown in FIG. 29(a) is performed (S345).

At this time, it is possible to simultaneously capture the color image and the black-and-white image using a single capturing unit through the adjustment of the illumination unit 16.

Subsequently, a step of determining whether the state of the acquired medicine image is good is performed (S347).

Step S347 is a step of determining whether the respective medicines in the acquired image have been captured to the extent that the medicines can be analyzed.

Upon determining at Step S347 that the acquired medicine image is not so good that the medicine image cannot be analyzed, a step of shaking the medicines from side to side or up and down to rearrange the medicines is performed (S349).

It is possible to rearrange the overlapped medicines or the medicines placed in incorrect capturing directions through Step S349.

Subsequently, an image analysis step of analyzing the acquired medicine image and extracting the respective medicines into independent regions is performed (S350).

Figure 30:
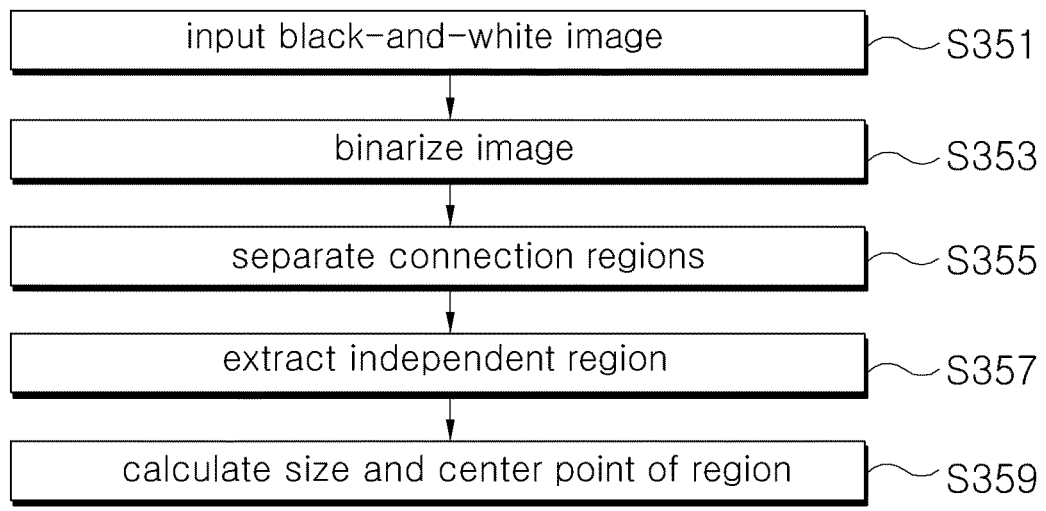

FIG. 30 is a detailed flow chart of Step S350. A step of inputting a black-and-white image of the compound medicines is performed (S351).

FIG. 31(a) is a view illustrating an embodiment of the black-and-white image of the compound medicines input at Step S351.

Subsequently, a step of creating a binarized image using a critical value of the black-and-white image is performed (S353).

At Step S353, the critical value is a reference pixel value for binarizing the black-and-white image.

Subsequently, a step of separating the binarized image into medicine connection regions is performed (S355).

In this embodiment of the present invention, Step S355 is performed using a method of extracting a circular image having a predetermined section from the center of each corner of the binarized image and measuring the area of the image and the angle of a separation line to distinguish joint corners of the medicines.

Subsequently, a step of extracting an independent region per medicine is performed (S357).

FIG. 31(b) is a view illustrating an embodiment of an image in which the compound medicines are divided into their independent regions at Step S357.

Subsequently, a step of deriving the size, center point and quantity of the independent region of each medicine is performed (S359).

Subsequently, a step of determining whether the size and quantity of the medicines derived through the image analysis at Step S350 coincide with medicine size and quantity of the medicine compounding information is performed (S360).

Upon determining at Step S360 that the size and quantity of the medicines derived through the image analysis at Step S350 do not coincide with the medicine size and quantity of the medicine compounding information, a step of creating a defective state indicating label is performed (S395).

On the other hand, upon determining at Step S360 that the size and quantity of the medicines derived through the image analysis at Step S350 coincide with the medicine size and quantity of the medicine compounding information, a medicine pattern analysis step of determining whether the pattern information of the captured medicines coincides with the medicine pattern information of the medicine compounding information is performed (S370).

Figure 32:
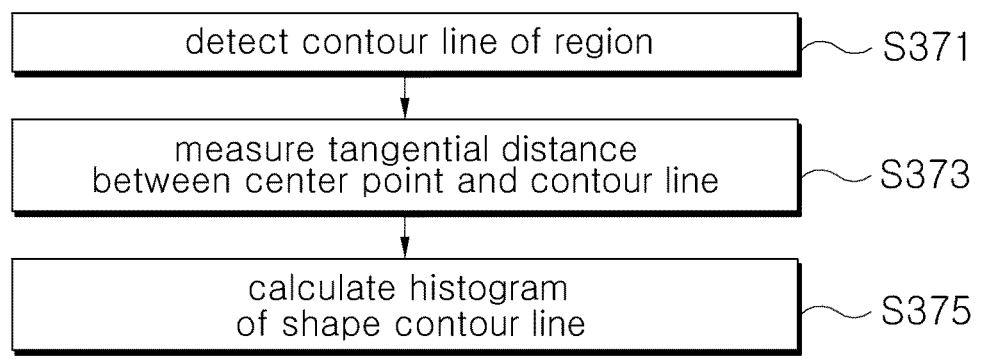

FIG. 32 is a detailed flow chart of Step S370. A step of detecting a contour line of an independent region of a medicine is performed (S371).

FIG. 25 is a view illustrating an embodiment of the medicine pattern analysis image at Step S370. At Step S371, it is possible to detect a contour line as shown in FIG. 25(b) from an independent region image as shown in FIG. 25(a).

Subsequently, a step of measuring the tangential distance between the contour line and the center point of the medicine as shown in FIG. 25(c) is performed (S373).

Subsequently, a step of calculating a histogram of the contour line of the medicine as shown in FIG. 25(d) is performed (S375).

Subsequently, a step of determining whether the histogram information of the medicine coincides with the medicine information of the medicine compounding information is performed (S380).

Upon determining at Step S380 that the oval medicine used in this embodiment of the present invention coincides with the medicine stored in the medicine pattern storage unit as shown in FIG. 26(b), a step of determining whether the medicine stored in the medicine pattern storage unit as shown in FIG. 26(b) coincides with the medicine compounding information is performed.

Subsequently, upon determining that the histogram information of the medicine coincides with the medicine information of the medicine compounding information, a step of creating a normal state indicating label using the label creation unit 90 is performed (S391).

Subsequently, a step of attaching the normal state indicating label or the defective state indicating label is performed (S397).

In this embodiment of the present invention, both the normal state indicating label and the defective state indicating label are created. According to circumstances, either the normal state indicating label or the defective state indicating label may be created and attached.

When the normal state indicating label or the defective state indicating label is attached to each sheet of medicine packaging paper, it is possible to easily identify the medicine compounding state.

When the compounding medicines are tested through Step S300 of the present invention as described above, it is possible to detect defective medicines through accurate and rapid medicine testing, thereby reducing a defect ratio of medicine compounding and improving efficiency of compound medicine management.

In the medicine image capturing device according to the present invention, as described above, a camera is installed in a camera tube, thereby acquiring a good-quality medicine image and easily determining and adjusting camera setting values.

Also, a reflection plate is provided at a refraction plane of the camera tube to secure the working distance between a medicine loading table and the camera, thereby preventing distortion of a medicine shape which occurs when the working distance is short.

Also, a camera module is configured in a bent shape such that the camera module can be installed in a limited equipment space, thereby improving spatial utilization.

Also, a correction panel is further provided to easily standardize camera setting values.

Also, a jig block is included in the correction panel, thereby easily testing the camera setting values.

Also, a center jig block and an auxiliary jig block are included in the correction panel, thereby easily analyzing camera setting elements at each position.

Also, a camera setting unit is further included to test and adjust the camera setting elements.

Also, the medicine image capturing device is capable of analyzing a focus, an image center axis, an image scale, and intensity of the camera.

In the medicine management system according to the present invention, as described above, it is possible to calculate and manage medicine pattern information based on medicine image analysis, thereby efficiently managing a large amount of medicine information, and to determine whether compound medicines are normal, thereby decreasing a defect rate of medicine compounding and improving management of the compound medicines.

Also, a medicine shift arrangement unit is further included to adjust positions or directions of medicines, thereby providing a function to capture the medicines in various directions and rapidly performing barcode recognition, capturing of compound medicines, and label attachment.

Also, basic medicine information, pattern information and medicine image information are stored in a storage unit, thereby configuring systematic medicine information.

Also, it is possible for the medicine management system to analyze various medicine pattern elements, such as external shape, color, marking, external dimensions, etc.

Also, a basic information input unit is further included to provide a function to input basic information of medicines.

Also, a medicine information retrieval unit is further included to easily retrieve basic medicine information using medicine pattern information.

Also, an identification code recognition unit is further included to recognize an identification code formed on compound medicine packaging paper, thereby improving efficiency in retrieval of medicine compounding information of medicines.

Also, it is possible for the medicine management system to analyze a captured image of a single medicine package, thereby deriving pattern information per medicine.

Also, it is possible for the medicine management system to analyze and store basic information and pattern information per medicine and compare pattern information of the captured medicine image with the pattern information per medicine, thereby determining whether compound medicines are defective.

Also, a label creation unit is further included to create and attach a label indicating whether a compound medicine per package is abnormal, thereby easily recognizing defective compound medicines.

Also, it is possible for the medicine management system to determine whether compound medicines are defective based on various kinds of information, such as size, quantity and shape, of medicines, thereby improving accuracy of compound medicine testing.

Also, a rearrangement unit for shaking overlapped medicines or the medicines placed in incorrect capturing directions in each medicine package to rearrange the overlapped medicines or the medicines placed in incorrect capturing directions is included in the medicine shift arrangement unit.

In the medicine management method according to the present invention, as described above, it is possible to perform a medicine pattern information registration operation using a medicine image, thereby improving medicine information management, and is capable of determining whether compound medicines are defective, thereby reducing time necessary to test the compound medicines and improving accuracy of testing.

Also, it is possible for the medicine management method to synchronize the camera setting of the medicine image of the medicine information management system and the automatic compound medicine test system, thereby improving efficiency and accuracy of medicine image processing.

Also, it is possible for the medicine management method to set components of an image capturing device unit in advance.

Also, it is possible for the medicine management method to extract a jig block from a collected correction panel image.

Also, it is possible for the medicine management method to measure the center coordinates and scale of a center jig block.

Also, it is possible for the medicine management method to test intensity of a correction panel image using an auxiliary jig block.

Also, it is possible for the medicine management method to compare a medicine image with a correction panel image, thereby determining whether defined camera setting values are proper.

Also, it is possible for the medicine management method to acquire a color image and a black-and-white image using a single capturing unit by adjusting brightness of illumination.

Also, it is possible for the medicine management method to calculate pattern information based on shapes of the medicines and express the calculated pattern information of the medicines as a graph or a shape code which is visually distinguishable.

Also, it is possible for the medicine management method to register medicine images captured in various directions, thereby improving accuracy in retrieval of medicine information.

Also, it is possible for the medicine management method to register medicine information of medicines cut into various sizes, thereby improving accuracy of medicine information retrieval.

Also, it is possible for the medicine management method to recognize an identification code formed on an individual medicine package, thereby easily retrieving medicine compounding information.

Also, it is possible for the medicine management method to create a black-and-white medicine image as well as a color medicine image, thereby easily analyzing individual regions of the medicines.

Also, it is possible for the medicine management method to analyze a medicine image into independent regions of individual medicines, thereby easily deriving pattern information of the individual medicines.

Also, it is possible for the medicine management method to derive and compare histogram information of the captured medicines based on external shape thereof with medicine compounding information, thereby improving objectivity of compound medicine testing.

Also, it is possible for the medicine management method to attach a defective state indicating label, upon determining that the size and quantity of the captured medicine or the histogram information of the captured medicines based on external shape thereof does not coincide with the medicine compounding information, thereby easily recognizing defective medicines.

Also, the medicine management method further includes an illumination adjusting step, thereby easily recognizing an identification code formed on medicine packaging paper.

Also, the medicine management method further includes a step of confirming a captured state of the acquired medicine image to rearrange medicines analysis of which is not possible, thereby improving efficiency and accuracy of image analysis.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A non-transitory machine readable medium that stores a program that, when executed by a processor, performs medicine management operations comprising:
   setting a camera of an image capturing device unit by:
      extracting a jig block from a medicine image captured by the image capturing device unit;
      analyzing image elements of the jig block; and
      setting a capturing mode of the camera;
   registering medicine information of the medicine image captured by the image capturing device unit; and
   comparing medicine information of a compound medicine image captured by the image capturing device unit with registered medicine information to determine whether the compound medicine is abnormal by:
      recognizing an identification code per medicine package;
      retrieving medicine compounding information from a medicine compounding information server;
      confirming medicine pattern information of a medicine pattern analysis unit based on the medicine compounding information;
      capturing an image of the compound medicine per package using an image processing unit and collecting the captured medicine image;
      analyzing the collected medicine image to extract medicines into independent regions; and
      determining whether the captured medicine pattern information coincides with medicine pattern information of the medicine compounding information using a medicine pattern analysis unit by:
         detecting a contour line of an independent medicine region from the medicine image;
         measuring a tangential distance between the contour line and a center point of the medicine;
         calculating a histogram of the contour line of the medicine; and
         determining whether the histogram information of the medicine coincides with medicine information of the medicine compounding information.

2. The non-transitory machine readable medium of claim 1, wherein the extracting the jig block from the collected medicine image comprises:
   extracting a center jig block from a correction panel; and
   extracting an auxiliary jig block from the correction panel,
   wherein the extracting the center jig block from the correction panel and the extracting the auxiliary jig block from the correction panel are sequentially or simultaneously performed.

3. The non-transitory machine readable medium of claim 1, wherein the analyzing the image elements of the jig block comprises measuring center coordinates and size of a center jig block, or measuring intensity of an auxiliary jig block.

4. The non-transitory machine readable medium of claim 1, wherein the registering the medicine information of the captured medicine image comprises:
   capturing a medicine image using the image capturing device unit and acquiring the captured medicine image;
   analyzing the acquired medicine image using an image analysis unit;
   calculating medicine pattern information from the analyzed medicine image; and
   registering medicine information.

5. The non-transitory machine readable medium of claim 4, wherein the acquiring the medicine image comprises:
   acquiring a black-and-white medicine image;
   adjusting brightness of an illumination unit; and
   acquiring a color medicine image.

6. The non-transitory machine readable medium of claim 4, wherein the analyzing the medicine image comprises:
   adjusting the position of a medicine region on the medicine image;
   binarizing the medicine image; and
   extracting a contour line of the independent medicine region.

7. The non-transitory machine readable medium of claim 4, wherein the calculating the medicine pattern information comprises:
   calculating at least one selected from a group consisting of a color, a symbol mark, a shape and external dimensions of each of the medicines; and
   calculating a graph or a shape code based on the medicine pattern information.

8. The non-transitory machine readable medium of claim 1, wherein the capturing the image of the compound medicine per package and collecting the captured medicine image comprises:
   capturing and collecting a red, green and blue (RGB) image of the compound medicine;
   separating a blue (B) channel from the collected medicine image; and
   acquiring a black-and-white medicine image.

9. The non-transitory machine readable medium of claim 1, wherein the analyzing the collected medicine image comprises:
   inputting a black-and-white image of the compound medicine;
   creating a binarized image using a critical value;
   separating the binarized image into medicine connection regions;

extracting an independent region per medicine;
deriving a size, center point and quantity of the independent region; and
determining whether the size and quantity of the captured medicines coincide with medicine size and quantity of the medicine compounding information.

10. The non-transitory machine readable medium of claim 1, wherein the medicine management operations further comprise:
determining whether a captured state per medicine of the image is good, wherein the step of determining whether the captured state per medicine of the image is good is performed after the step of capturing the image of the compound medicine per package and collecting the captured medicine image; and
shaking the medicines from side to side or up and down to rearrange the medicines using a rearrangement unit upon determining that the medicine image state is not good, wherein the step of capturing the image of the compound medicine per package and collecting the captured medicine image is performed after the step of shaking the medicines from side to side or up and down to rearrange the medicines.

\* \* \* \* \*